(12) United States Patent
Hovanec

(10) Patent No.: US 7,267,816 B2
(45) Date of Patent: Sep. 11, 2007

(54) AMMONIA-OXIDIZING BACTERIA

(75) Inventor: Timothy A. Hovanec, Moorpark, CA (US)

(73) Assignee: Aquaria, Inc., Moorpark, CA (US)

( * ) Notice: Subject to any disclaimer, the term of this patent is extended or adjusted under 35 U.S.C. 154(b) by 521 days.

(21) Appl. No.: 10/659,983

(22) Filed: Sep. 10, 2003

(65) Prior Publication Data

US 2004/0157313 A1 Aug. 12, 2004

Related U.S. Application Data

(63) Continuation-in-part of application No. 09/573,684, filed on May 19, 2000, now abandoned.

(60) Provisional application No. 60/386,217, filed on Sep. 19, 2002, provisional application No. 60/386,218, filed on Sep. 19, 2002, provisional application No. 60/386,219, filed on Sep. 19, 2002.

(51) Int. Cl.
*C12P 1/20* (2006.01)

(52) U.S. Cl. ............... 424/93.4; 435/252.1; 435/252.4; 425/93.3; 536/23.1; 536/24.1

(58) Field of Classification Search ............... None
See application file for complete search history.

(56) References Cited

OTHER PUBLICATIONS

Tal, Yossi et al.; Characterization of the Microbial Community and Nitrogen Transformation Processes Associated with Moving Bed Bioreactors in a Closed Recirculated Mariculture System; Elsevier Science B.V., Aquaculture, 2003, pp. 187-202.

Teske et al.: "Evolutionary relationships among ammonia- and nitrite-oxidizing bacteria" Database:EBI Accession No. L35505 Date of Availability: Nov. 29, 1994.

Van Der Meer et al: "Characterization of the bacterial composition of a nitrogen-removing biofilm from a trickling filter at Kollikon, Switzerland" Database: EBI Accession No. AJ224941 Date of Availability: Mar. 13, 1998.

Purkhold et al.: "Comparative 16S rRNA and amoA sequence analysis: Implications for molecular diversity surveys" Database: EBI Accession No. AF272420 Date of Availability: Dec. 6, 2000.

Suwa et al.: "Phylogenetic relationships of activated sludge isolates of ammonia oxidizers with different sensitivities to ammonium sulfate," J Gen. Appl. Microbiol., vol. 43, pp. 373-379 (1997).

Suwa: "Nitrosomonas sp. JL21 gene for 16S rRNA, partial sequence" Database: EBI Accession No. AB000700 Date of Availability: May 5, 1998.

Head et al.: "The phylogeny of autotrophic ammonia-oxidizing bacteria as determined by analysis of 16S ribosomal RNA gene sequences," Journal of General Microbiology, vol. 139, pp. 1147-1153 (1993).

Stackenbrandt et al. (2001) Encyclopedia of Life Sciences, pp. 1-7, Nature Publishing Group, New York, NY.

Aakra, Agot et al., "RFLP of rRNA genes and sequencing of the 16S-23S rDNA intergenic spacer region of ammonia-oxidizing bacteria: a phylogenetic approach," Intl. Journal of Systematic Bacteriology, 1999, pp. 123-130.

Hovanec, Timothy et al., "Comparative Analysis of Nitrifying Bacteria Associate with Freshwater and Marine Aquaria," Applied and Environmental Microbiology, Aug. 1996, pp. 2888-2896.

Burrell, Paul C. et al., "Aquatic Nitrate Oxidising Microorganisms," Canadian Intellectual Property Office, Nov. 20, 1998, pp. 1-76.

*Primary Examiner*—Irene Marx
(74) *Attorney, Agent, or Firm*—Pillsbury Winthrop Shaw Pittman LLP

(57) ABSTRACT

Described herein are novel ammonia-oxidizing bacteria as well as isolated nucleotide sequences representative of 16S rDNA of these ammonia-oxidizing bacteria. Particular bacteria of the present invention are tolerant of freshwater environments, saltwater environments or both. Furthermore, in various embodiments, various bacteria of the present invention are capable of surviving a freeze-drying process, and may remain viable thereafter. Compositions including various combinations of the bacteria are further described, as are polymerase chain reaction (PCR) primers and oligonucleotide probes that may be used to detect these bacteria based on their 16S rDNA.

12 Claims, 10 Drawing Sheets

Figure 1. Phylogenetic relationship of the three bacterial strains and one substrain inferred from comparative analysis of 16S rDNA sequences. The tree is based on neighbour-joining distance analysis of sequences containing a minimum of 1430 nucleotides.

FIG. 2. Denaturing gradient gel electrophoresis (DGGE) of biomasses from selected cultures and ammonia-oxidizing bacteria described herein.

Mean ammonia trends (N=3) for aquaria dosed with AOB bacteria in accordance with an embodiment of the present invention or commercially available nitrifying bacteria mixtures.

Mean ammonia trends (N=4) for saltwater aquaria dosed with saltwater AOB bacteria in accordance with an embodiment of the present invention and control aquaria that were not dosed.

Mean ammonia trends (N=4) for aquaria dosed with saltwater bacteria in accordance with an embodiment of the present invention and control aquaria that were not dosed.

SEQUENCE LISTING

```
<160> NUMBER OF SEQ ID NOS: 23

<210> SEQ ID NO 1
<211> LENGTH: 1457
<212> TYPE: DNA
<213> ORGANISM: Unknown
<220> FEATURE:
<223> OTHER INFORMATION: AOB Type A R7clone140 16S rDNA

<400> SEQUENCE: 1
attgaacgct ggcggcatgc tttacacatg caagtcgaac ggcagcacgg atgcttgcat      60
ctggtggcga gtggcggacg ggtgagtaat gcatcggaac gtatccagaa gagggggta     120 acgcatcgaa agatgtgcta ataccgcata tactctaagg aggaaagcag gggatcgaaa    180
gaccttgcgc ttttggagcg gccgatgtct gattagctag ttggtggggt aaaggcctac    240
caaggcgacg atcagtagtt ggtctgagag gacgaccagc cacactggga ctgagacacg    300
gcccagactc ctacgggagg cagcagtggg gaattttgga caatgggcgc aagcctgatc    360
cagcaatgcc gcgtgagtga agaaggcctt cgggttgtaa agctctttca gtcgagaaga    420
aaaggttacg gtaaataatc gtgactcatg acggtatcga cagaagaagc accggctaac    480
tacgtgccag cagccgcggt aatacgtagg gtgcaagcgt taatcggaat tactgggcgt    540
aaagggtgcg caggcggctt tgtaagtcag atgtgaaatc cccgggctta acctgggaat    600
tgcgtttgaa actacaaggc tagagtgtgg cagagggagg tggaattcca tgtgtagcag    660
tgaaatgcgt agagatatgg aagaacatcg atggcgaagg cagcctcctg ggttaacact    720
gacgctcatg cacgaaagcg tggggagcaa acaggattag ataccctggt agtccacgcc    780
ctaaacgatg tcaactagtt gttgggcctt attaggcttg gtaacgaagc taacgcgtga    840
agttgaccgc ctggggagta cggtcgcaag attaaaactc aaaggaattg acggggaccc    900
gcacaagcgg tggattatgt ggattaattc gatgcaacgc gaaaaacctt acctacccttt    960 gacatgtagc gaattttcta gagatagatt agtgcttcgg gaacgctaac acaggtgctg   1020
catggctgtc gtcagctcgt gtcgtgagat gttgggttaa gtcccgcaac gagcgcaacc   1080
cttgtcatta attgccatca tttggttggg cactttaatg agactgccgg tgacaaaccg   1140
gaggaaggtg gggatgacgt caagtcctca tggcccttat gggtagggct tcacacgtaa   1200
tacaatggcg cgtacagagg gttgccaacc cgcgaggggg agctaatctc agaaagcgcg   1260
tcgtagtccg gatcggagtc tgcaactcga ctccgtgaag tcggaatcgc tagtaatcgc   1320
ggatcagcat gtcgcggtga atacgttccc gggtcttgta cacaccgccc gtcacaccat   1380
gggagtgggt tcaccagaa gcaggtagtc taaccgtaag gagggcgctt gccacggtga   1440
gattcatgac tgggtg                                                    1457
```

```
<210> SEQ ID NO 2
<211> LENGTH: 1457
<212> TYPE: DNA
<213> ORGANISM: Unknown
<220> FEATURE:
<223> OTHER INFORMATION: AOB Type A1 R7clone187 16S rDNA

<400> SEQUENCE: 2
attgaacgct ggcggcatgc tttacacatg caagtcgaac ggcagcacgg atgcttgcat    60
ctggtggcga gtggcggacg ggtgagtaat gcatcggaac gtatccagaa gagggggta   120 acgcatcgaa agatgtgcta ataccgcata tactctaagg aggaaagcag gggatcgaaa   180
gaccttgcgc ttttggagcg gccgatgtct gattagctag ttggtggggt aaaggcctac   240
caaggcgacg atcagtagtt ggtctgagag gacgaccagc cacactggga ctgagacacg   300
gcccagactc ctacgggagg cagcagtggg gaattttgga caatgggcgc aagcctgatc   360
cagcaatgcc gcgtgagtga agaaggcctt cgggttgtaa agctctttca gtcgagaaga   420
aaaggttacg gtaaataatc gtgacccatg acggtatcga cagaagaagc accggctaac   480
tacgtgccag cagccgcggt aatacgtagg gtgcaagcgt taatcggaat tactgggcgt   540
aaagggtgcg caggcggcct tgtaagtcag atgtgaaatc cccggctta acctgggaat   600 tgcgtttgaa actacaaagc tagagtgtgg cagaggagg tggaattcca tgtgtagcag   660
tgaaatgcgt agagatatgg aagaacatcg atggcgaagg cagcctcctg ggttaacact   720
gacgctcatg cacgaaagcg tggggagcaa acaggattag ataccctggt agtccacgcc   780
ctaaacgatg tcaactagtt gttgggcctt attaggcttg gtaacgaagc taacgcgtga   840
agttgaccgc ctgggagta cggtcgcaag attaaaactc aaaggaattg acggggaccc   900
gcacaagcgg tggattatgt ggattaattc gatgcaacgc gaaaaacctt acctacccctt   960 gacatgtagc gaattttcta gagatagatt agtgcttcgg gaacgctaac acaggtgctg  1020
catggctgtc gtcagctcgt gtcgtgagat gttgggttaa gtcccgcaac gagcgcaacc  1080
cttgtcatta attgccatca tttggttggg cactttaatg agactgccgg tgacaaaccg  1140
gaggaaggtg gggatgacgt caagtcctca tggcccttat gggtagggct tcacacgtaa  1200
tacaatggcg cgtacagagg gttgccaacc cgcgagggg agctaatctc agaaagcgcg  1260
tcgtagtccg gatcggagtc tgcaactcga ctccgtgaag tcggaatcgc tagtaatcgc  1320
ggatcagcat gtcgcggtga atacgttccc gggtcttgta cacaccgccc gtcacaccat  1380
gggagtgggt ttcaccagaa gcaggtagtc taaccgtaag gagggcgctt gccacggtga  1440
gattcatgac tggggtg                                                 1457

<210> SEQ ID NO 3
<211> LENGTH: 1458
<212> TYPE: DNA
<213> ORGANISM: Unknown
<220> FEATURE:
<223> OTHER INFORMATION: AOB Type B R3clone5 16S rDNA

<400> SEQUENCE: 3
attgaacgct ggcggcatgc tttacacatg caagtcgaac ggcagcacgg gggcaaccct    60
ggtggcgagt ggcgaacggg tgagtaatac atcggaacgt atcttcgagg ggggataac   120 gcaccgaaag gtgtgctaat accgcataat ctccacggag aaaagcaggg gatcgcaaga   180
ccttgcgctc ttggagcggc cgatgtctga ttagctagtt ggtgaggtaa tggcttacca   240
aggcgacgat cagtagctgg tctgagagga cgaccagcca cactgggact gagacacggc   300
```

| | |
|---|---|
| ccagactcct acggaggca gcagtgggga attttggaca atgggggaaa ccctgatcca | 360 |
| gccatgccgc gtgagtgaag aaggccttcg ggttgtaaag ctctttcagc cggaacgaaa | 420 |
| cggtcacggc taatacccgt gactactgac ggtaccggaa gaagaagcac cggctaacta | 480 |
| cgtgccagca gccgcggtaa tacgtagggt gcaagcgtta atcggaatta ctgggcgtaa | 540 |
| agcgtgcgca ggcggttttg taagtcagat gtgaaagccc cgggcttaac ctggaactg | 600 |
| cgtttgaaac tacaaggcta gagtgtgca gagggggtg gaattccacg tgtagcagtg | 660 |
| aaatgcgtag agatgtggag gaacaccgat ggcgaaggca gccccctggg ttaacaccga | 720 |
| cgctcaggca cgaaagcgtg gggagcaaac aggattagat accctggtag tccacgccct | 780 |
| aaacgatgtc aactagttgt cgggtcttaa cggacttggt aacgcagcta acgcgtgaag | 840 |
| ttggccgcct gggagtacg gtcgcaagat taaaactcaa aggaattgac ggggacccgc | 900 |
| acaagcggtg gattatgtgg attaattcga tgcaacgcga aaaaccttac ctacccttga | 960 |
| catgtaccga agcccgccga gaggtggtg tgcccgaaag ggagcggtaa cacaggtgct | 1020 |
| gcatggctgt cgtcagctcg tgtcgtgaga tgttgggtta agtcccgcaa cgagcgcaac | 1080 |
| ccttgtcatt aattgccatc attcagttgg cactttaat gaaactgccg gtgacaaacc | 1140 |
| ggaggaaggt ggggatgacg tcaagtcctc atggccctta tgggtagggc ttcacacgta | 1200 |
| atacaatggc gcgtacagag ggttgccaac ccgcgagggg gagctaatct cagaaagcgc | 1260 |
| gtcgtagtcc ggatcggagt ctgcaactcg actccgtgaa gtcggaatcg ctagtaatcg | 1320 |
| cggatcagca tgtcgcggtg aatacgttcc cgggtcttgt acacaccgcc cgtcacacca | 1380 |
| tgggagtggg tttcaccaga agcaggtagt ctaaccgcaa ggagggcgct tgccacggtg | 1440 |
| agattcatga ctgggggtg | 1458 |

<210> SEQ ID NO 4
<211> LENGTH: 1460
<212> TYPE: DNA
<213> ORGANISM: Unknown
<220> FEATURE:
<223> OTHER INFORMATION: AOB Type C R5clone47 16D rDNA

<400> SEQUENCE: 4

| | |
|---|---|
| attgaacgct ggcggcatgc tttacacatg caagtcgaac ggcagcgggg gcttcggcct | 60 |
| gccggcgagt ggcgaacggg tgagtaatac atcggaacgt gtccttaagt ggggaataac | 120 |
| gcatcgaaag atgtgctaat accgcatatc tctgaggaga aaagcagggg atcgcaagac | 180 |
| cttgcgctaa aggagcggcc gatgtctgat tagctagttg gtgggtaaa ggcttaccaa | 240 |
| ggcaacgatc agtagttggt ctgagaggac gaccaaccac actgggactg agacacggcc | 300 |
| cagactccta cgggaggcag cagtgggaa ttttggaca tgggcgaaag cctgatccag | 360 |
| ccatgccgcg tgagtgaaga aggccttcgg gttgtagagc tcttttagtc agaaagaaag | 420 |
| aatcatgatg aataattatg atttatgacg gtactgacga aaaagcacc ggctaactac | 480 |
| gtgccagcag ccgcggtaat acgtagggtg cgagcgttaa tcggaattac tgggcgtaaa | 540 |
| gggtgcgcag gcggttttgt aagtcagatg tgaaagcccc gggcttaacc tgggaattgc | 600 |
| gtttgaaact acaaggctag agtgcagcag aggggagtgg aattccatgt gtagcagtga | 660 |
| aatgcgtaga gatgtggaag aacaccgatg gcgaaggcag ctccctgggt tgacactgac | 720 |
| gctcatgcac gaaagcgtgg ggagcaaaca ggattagata ccctggtagt ccacgcccta | 780 |
| aacgatgtca actggttgtc ggatctaatt aaggatttgg taacgtagct aacgcgtgaa | 840 |
| gttgaccgcc tggggagtac ggtcgcaaga ttaaaactca aaggaattga cggggacccg | 900 |

```
cacaagcggt ggattatgtg gattaattcg atgcaacgcg aaaaacctta cctacccttg    960
acatgcttgg aatctagtgg agacataaga gtgcccgaaa gggagccaag acacaggtgc   1020
tgcatggctg tcgtcagctc gtgtcgtgag atgttgggtt aagtcccgca acgagcgcaa   1080
cccttgtcac taattgctat cattctaaat gagcacttta gtgagactgc cggtgacaaa   1140
ccggaggaag gtggggatga cgtcaagtcc tcatggccct tatgggtagg gcttcacacg   1200
taatacaatg gcgtgtacag agggttgcca acccgcgagg gggagccaat ctcagaaagc   1260
acgtcgtagt ccggatcgga gtctgcaact cgactccgtg aagtcggaat cgctagtaat   1320
cgcggatcag catgccgcgg tgaatacgtt cccgggtctt gtacacaccg cccgtcacac   1380
catgggagtg gttttcacca gaagcaggta gtttaaccgt aaggaggacg cttgccacgg   1440
tgggggtcat gactggggtg                                                1460
```

```
<210> SEQ ID NO 5
<211> LENGTH: 18
<212> TYPE: DNA
<213> ORGANISM: Artificial
<220> FEATURE:
<223> OTHER INFORMATION: Oligonucleotide Probe

<400> SEQUENCE: 5
cccccctctt ctggatac                                                   18

<210> SEQ ID NO 6
<211> LENGTH: 18
<212> TYPE: DNA
<213> ORGANISM: Artificial
<220> FEATURE:
<223> OTHER INFORMATION: PCR Primer

<400> SEQUENCE: 6
cggaacgtat ccagaaga                                                   18

<210> SEQ ID NO 7
<211> LENGTH: 18
<212> TYPE: DNA
<213> ORGANISM: Artificial
<220> FEATURE:
<223> OTHER INFORMATION: PCR Primer

<400> SEQUENCE: 7
atctctagaa aattcgct                                                   18

<210> SEQ ID NO 8
<211> LENGTH: 19
<212> TYPE: DNA
<213> ORGANISM: Artificial
<220> FEATURE:
<223> OTHER INFORMATION: Oligonucleotide Probe

<400> SEQUENCE: 8
tcccccactc gaagatacg                                                  19

<210> SEQ ID NO 9
<211> LENGTH: 17
<212> TYPE: DNA
<213> ORGANISM: Artificial
<220> FEATURE:
<223> OTHER INFORMATION: PCR Primer

<400> SEQUENCE: 9
```

```
atcggaacgt atcttcg                                              17
```

<210> SEQ ID NO 10
<211> LENGTH: 16
<212> TYPE: DNA
<213> ORGANISM: Artificial
<220> FEATURE:
<223> OTHER INFORMATION: PCR Primer

<400> SEQUENCE: 10

```
ccacctctcr gcgggc                                               16
```

<210> SEQ ID NO 11
<211> LENGTH: 19
<212> TYPE: DNA
<213> ORGANISM: Artificial
<220> FEATURE:
<223> OTHER INFORMATION: PCR Primer

<400> SEQUENCE: 11

```
tcagaaagaa agaatcatg                                            19
```

<210> SEQ ID NO 12
<211> LENGTH: 19
<212> TYPE: DNA
<213> ORGANISM: Artificial
<220> FEATURE:
<223> OTHER INFORMATION: PCR Primer

<400> SEQUENCE: 12

```
gtctccayta gattccaag                                            19
```

<210> SEQ ID NO 13
<211> LENGTH: 17
<212> TYPE: DNA
<213> ORGANISM: Artificial
<220> FEATURE:
<223> OTHER INFORMATION: PCR Primer

<400> SEQUENCE: 13

```
gtttgatcct ggctcag                                              17
```

<210> SEQ ID NO 14
<211> LENGTH: 19
<212> TYPE: DNA
<213> ORGANISM: Artificial
<220> FEATURE:
<223> OTHER INFORMATION: PCR Primer

<400> SEQUENCE: 14

```
ggttaccttg ttacgactt                                            19
```

<210> SEQ ID NO 15
<211> LENGTH: 17
<212> TYPE: DNA
<213> ORGANISM: Artificial
<220> FEATURE:
<223> OTHER INFORMATION: PCR Primer

<400> SEQUENCE: 15

```
cctacgggag gcagcag                                              17
```

<210> SEQ ID NO 16
<211> LENGTH: 18
<212> TYPE: DNA
<213> ORGANISM: Artificial

<220> FEATURE:
<223> OTHER INFORMATION: PCR Primer

<400> SEQUENCE: 16
gwattaccgc ggckgctg                                                 18

<210> SEQ ID NO 17
<211> LENGTH: 20
<212> TYPE: DNA
<213> ORGANISM: Artificial
<220> FEATURE:
<223> OTHER INFORMATION: PCR Primer

<400> SEQUENCE: 17
cactctagcy ttgtagtttc                                               20

<210> SEQ ID NO 18
<211> LENGTH: 1467
<212> TYPE: DNA
<213> ORGANISM: Unknown
<220> FEATURE:
<223> OTHER INFORMATION: N. Aestuarii-like AOB P4clone42 16S rDNA

<400> SEQUENCE: 18
ttgatcatgg ctcagattga acgctggcgg catgctttac acatgcaagt cgaacggcag     60
cacgggtgct tgcacctggt ggcgagtggc ggacgggtga gtaatgcatc ggaacgtgtc    120
cagaagtggg ggataacgca tcgaaagatg tgctaatacc gcatattctc tacggaggaa    180
agcagggat cgaaagacct tgtgcttttg gagcggccga tgcctgatta gctagttggt    240
ggggtaaagg cctaccaagg caacgatcag tagttggtct gagaggacga ccagccacac    300
tgggactgag acacggccca gactcctacg ggaggcagca gtggggaatt ttggacaatg    360
ggcgaaagcc tgatccagca atgccgcgtg agtgaagaag cttcgggtt gtaaagctct    420
ttcagtcgag aagaaaaggt tgtgactaat aatcacaact tatgatggta ccgacagaag    480
aagcaccggc taactacgtg ccagcagccg cggtaatacg tagggtgcaa gcgttaatcg    540
gaattactgg gcgtaaaggg tgcgcaggcg gctttgtaag tcagatgtga atccccggg    600
cttaacctgg gaattgcgtt tgaaactaca agctagagt gtagcagagg ggggtggaat    660
tccatgtgta gcagtgaaat gcgtagagat atggaagaac atcgatggcg aaggcagccc    720
cctgggttaa cactgacgct catgcacgaa agcgtgggga gcaaacagga ttagatacc    780
tggtagtcca cgccctaaac gatgtcaact agttgttggg ccttactagg cttggtaacg    840
tagctaacgc gtgaagttga ccgcctgggg agtacggtcg caggattaaa actcaaagga    900
attgacgggg acccgcacaa gcggtggatt atgtggatta attcgatgca acgcgaaaaa    960
ccttacctac ccttgacatg tagcgaatat tttagagata aaatagtgcc ttcgggaacg   1020
ctaacacagg tgctgcatgg ctgtcgtcag ctcgtgtcgt gagatgttgg gttaagtccc   1080
gcaacgagcg caaccttgt cattaattgc catcatttag ttgggcactt taatgagact   1140
gccggtgaca aaccggagga aggtggggat gacgtcaagt cctcatggcc cttatgggta   1200
gggcttcaca cgtaatacaa tggcgcgtac agagggttgc caacccgcga gggggagcta   1260
atctcagaaa gcgcgtcgta gtccggatcg gagtctgcaa ctcgactccg tgaagtcgga   1320
atcgctagta atcgcggatc agcatgtcgc ggtgaatacg ttcccgggtc ttgtacacac   1380
cgcccgtcac accatgggag tgggtttcac cagaagcaga tagtctaacc gtaagagggc   1440
gtttgccacg gcgagattca tgactgg                                     1467

<210> SEQ ID NO 19
<211> LENGTH: 1494
<212> TYPE: DNA
<213> ORGANISM: Unknown
<220> FEATURE:
<223> OTHER INFORMATION: N. Aestuarii-like AOB P4clone31 16S rDNA

<400> SEQUENCE: 19

| | | | | |
|---|---|---|---|---|
| agtttgatca | tggctcagat | tgaacgctgg | cggcatgctt | tacacatgca agtcgaacgg | 60 |
| cagcacgggt | gcttgcacct | ggtggcgagt | ggcggacggg | tgagtaatgc atcggaacgt | 120 |
| gtccggaagt | gggggataac | gcatcgaaag | atgtgctaat | accgcatatt ctctacggag | 180 |
| gaaagcaggg | gatcgaaaga | ccttgtgctt | ttggagcggc | cgatgcctga ttagctagtt | 240 |
| ggtgggtaa | aggcctacca | aggcaacgat | cagtagttgg | tctgagagga cgaccagcca | 300 |
| cactgggact | gagacacggc | ccagactcct | acgggaggca | gcagtgggga attttggaca | 360 |
| acgggcgaaa | gcctgatcca | gcaatgccgc | gtgagtgaag | aaggccttcg ggttgtaaag | 420 |
| ctctttcagt | cgagaagaaa | aggttgtgac | taataatcac | aacttatgac ggtaccgaca | 480 |
| gaagaagcac | cggctaacta | cgtgccagca | gccgcggtaa | tacgtagggt gcaagcgtta | 540 |
| atcggaatta | ctgggcgtaa | agggtgcgca | ggcggctttg | taagtcagat gtgaaatccc | 600 |
| cgggcttaac | ctgggaattg | cgtttgaaac | tacaaagcta | gagtgtagca gagggggtg | 660 |
| gaattccatg | tgtagcagtg | aaatgcgtag | agatatggaa | gaacatcgat ggcgaaggca | 720 |
| gccccctggg | ttaacactga | cgctcatgca | cgaaagcgtg | gggagcaaac aggattagat | 780 |
| accctggtag | tccacgcect | aaacgatgtc | aactagttgt | tgggccttac taggcttggt | 840 |
| aacgtagcta | acgcgtgaag | ttgaccgcct | ggggagtacg | gtcgcaagat taaaactcaa | 900 |
| aggaattgac | ggggacccgc | acaagcggtg | gattatgtgg | attaattcga tgcaacgcga | 960 |
| aaaaccttac | ctaccttga | catgtagcga | atattttaga | gataaaatag tgccttcggg | 1020 |
| aacgctaaca | caggtgctgc | atggctgtcg | tcagctcgtg | tcgtgagatg ttgggttaag | 1080 |
| tcccgcaacg | agcgcaaccc | ttgtcattaa | ttgccatcat | ttagttgggc actttaatga | 1140 |
| gactgccggt | gacaaaccgg | aggaaggtgg | ggatgacgtc | aagtcctcat ggcccttatg | 1200 |
| ggtagggctt | cacacgtaat | acaatggcgc | gtacagaggg | ttgccaaccc gcgaggggga | 1260 |
| gctaatctca | gaaagcgcgt | cgtagtccgg | atcggagtta | gcaactcgac tccgtgaagt | 1320 |
| cggaatcgct | agtaatcgcg | gatcagcatg | tcgcggtgaa | tacgttcccg ggccttgtac | 1380 |
| acaccgcccg | tcacaccatg | gaagttggct | gcaccagaag | taggttgtct aaccctcggg | 1440 |
| aggacgctta | ccacggtgtg | gtcaatgact | ggggtgaag | tcgtaacaag gtaa | 1494 |

<210> SEQ ID NO 20
<211> LENGTH: 1491
<212> TYPE: DNA
<213> ORGANISM: Unknown
<220> FEATURE:
<223> OTHER INFORMATION: N. Aestuarii-like AOB BF16clone57 16S rDNA

<400> SEQUENCE: 20

| | | | | |
|---|---|---|---|---|
| gtttgatcat | ggctcagatt | gaacgctggc | ggcatgcttt | acacatgcaa gtcgaacggc | 60 |
| agcacgggtg | cttgcacctg | gtggcgagtg | cggacgggt | gagtaatgca tcggaacgtg | 120 |
| tccagaagtg | ggggataacg | catcgaaaga | tgtgctaata | ccgcatattc tctacggagg | 180 |
| aaagcagggg | atcgaaagac | cttgtgcttt | tggagcggcc | gatgcctgat tagctagttg | 240 |
| gtggggtaaa | ggcctaccaa | ggcaacgatc | agtagttggt | ctgagaggac gaccagccac | 300 |

-continued

```
actgggactg agacacggcc cagactccta cgggaggcag cagtggggaa ttttggacaa    360
tgggcgaaag cctgatccag caatgccgcg tgagtgaaga aggccttcgg gttgtaaagc    420
tctttcagtc gagaagaaaa ggttgtgact aataatcaca acttatgacg gtaccgacag    480
aagaagcacc ggctaactac gtgccagcag ccgcggtaat acgtagggtg caagcgttaa    540
tcggaattac tgggcgtaaa gggtgcgcag gcggctttgt aagtcagatg tgaaatcccc    600
gggcttaacc tggaattgc gtttgaaact acaaagctag agtgtagcag agggggggtgg    660 aattccatgt gtagcagtga atgcgtaga gatatggaag aacatcgatg gcgaaggcag    720 cccctggt taacactgac gctcatgcac gaaagcgtgg ggagcaaaca ggattagata    780
ccctggtagt ccacgcccta acgatgtca actagttgtt gggccttact aggcttggta    840
acgtagctaa cgcgtgaagt tgaccgcctg gggagtacgg tcgcaagatt aaaactcaaa    900
ggaattgacg ggacccgca caagcggtgg attatgtgga ttaattcgat gcaacgcgaa    960
aaaccttacc taccttgac atgtagcgaa tatttagag ataaaatagt gccttcggga    1020
acgctaacac aggtgctgca tggctgtcgt cagctcgtgt cgtgagatgt tgggttaagt    1080
cccgcaacga gcgcaaccct tgtcattaat tgccatcatt tagttgggca ctttaatgag    1140
actgccggtg acaaaccgga ggaaggtggg gatgacgtca agtcctcatg gcccttatgg    1200
gtagggcttc acacgtaata caatggcgcg tacagagggt tgccaacccg cgaggggag    1260 ctaatctcag aaagcgcgtc gtagtccgga tcggagtctg caactcgact ccgtgaagtc    1320
ggaatcgcta gtaatcgcgg atcagcatgt cgcggtgaat acgttcccgg gtcttgtaca    1380
caccgcccgt cacaccatgg gagtgggttt caccagaagc agatagtcta accgtaagga    1440
gggcgtttgc cacggtgaga ttcatgactg gggtgaagtc gtaacaattt a             1491
```

<210> SEQ ID NO 21
<211> LENGTH: 18
<212> TYPE: DNA
<213> ORGANISM: Artificial
<220> FEATURE:
<223> OTHER INFORMATION: Oligonucleotide Probe

<400> SEQUENCE: 21

```
tcccccactt ctggacac                                                   18
```

<210> SEQ ID NO 22
<211> LENGTH: 21
<212> TYPE: DNA
<213> ORGANISM: Artificial
<220> FEATURE:
<223> OTHER INFORMATION: PCR Primer

<400> SEQUENCE: 22

```
gtgactaata atcacaactt a                                               21
```

<210> SEQ ID NO 23
<211> LENGTH: 20
<212> TYPE: DNA
<213> ORGANISM: Artificial
<220> FEATURE:
<223> OTHER INFORMATION: PCR Primer

<400> SEQUENCE: 23

```
ttatctctaa aatattcgct                                                 20
```

AMMONIA-OXIDIZING BACTERIA

This is a Continuation-in-Part of U.S. patent application Ser. No. 09/573,684, filed May 19, 2000, now abandoned, which is incorporated herein in its entirety. This application claims the benefit of priority under 35 U.S.C. § 119 of provisional U.S. application Ser. No. 60/386,217, filed Sep. 19, 2002, provisional U.S. application Ser. No. 60/386,218, filed Sep. 19, 2002 and provisional U.S. application Ser. No. 60/386,219, filed Sep. 19, 2002, the contents of all of which are hereby incorporated by reference.

FIELD OF THE INVENTION

The invention relates generally to ammonia oxidizers and specifically to bacteria capable of oxidizing ammonia to nitrite.

BACKGROUND OF THE INVENTION

Ammonia is the principal nitrogenous waste product of teleosts and many invertebrates in both freshwater and seawater. The ammonia results from the deamination or transamination of proteins the organism receives via its diet. However, high ammonia concentrations can be toxic to many of these same aquatic organisms. In natural systems, such as lakes, rivers and oceans, the concentration of ammonia rarely reaches deleterious levels because the density of fish (and other organisms) per mass of water is low.

However, in man-made aquatic systems such as aquaculture rearing pens, tanks, raceways and ponds plus aquaria, both public and private, ammonia can reach toxic concentrations, sometimes very quickly. One reason for this is that in the above-named systems the fish density can be very large in relation to the small amount of water. Another reason is that in many of these systems the water is not continually changed; rather it recirculates through the system with only periodic partial water changes.

Therefore, most aquaculture systems and aquaria use filtration, in one form or another, to maintain a degree of water quality that is suitable for the maintenance and growth of aquatic organisms. A major component of any such filtration unit is the biological filter. The biological filter gets its name from the fact that it acts as a substrate or site for the growth of bacteria which have the capability to convert, by way of oxidation, ammonia to another compound—nitrite. High concentrations of nitrite can also be toxic but there are other species of bacteria which grow on the biological filter and oxidize the nitrite to nitrate, such as those described in U.S. Pat. Nos. 6,268,154, 6,265,206 and 6,207,440, each of which is incorporated by reference herein in its entirety as if fully set forth. Nitrate is considered non-toxic to aquatic organisms except in extreme cases of very high concentrations.

There are other situations or applications which use biological filters. These include sewage treatment facilities, wastewater treatment facilities and drinking water filtration plants. While each will have its own particular reason for using a biological filter, the goal is the same: the conversion of toxic inorganic nitrogen compounds to less harmful inorganic nitrogen substances. Biological filtration is necessary for many facilities to meet the National Recommended Water Quality Criteria as set by the Environmental Protection Agency (EPA) of the United States of America.

The oxidation of ammonia to nitrite is a bacterially-mediated process. Specifically, it is a two step oxidation process involving the conversion of ammonia to nitrite according to the following equations:

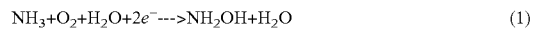

$$NH_3 + O_2 + H_2O + 2e^- \longrightarrow NH_2OH + H_2O \qquad (1)$$

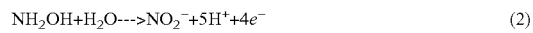

$$NH_2OH + H_2O \longrightarrow NO_2^- + 5H^+ + 4e^- \qquad (2)$$

The most commonly studied ammonia oxidizing bacteria (AOB) is *Nitrosomonas europaea*. It was originally isolated from soils and is purported to be the active AOB in aquaculture facilities (Wheaton, F. W. 1977. Aquacultural Engineering. John Wiley & Sons, Inc. New York.), in wastewater treatment facilities (Painter, H. A. 1986. Nitrification in the treatment of sewage and waste-waters. In Nitrification J. I. Prosser ed. IRL Press. Oxford.) and in aquaria (Spotte, S. 1979. Seawater Aquariums—The Captive Environment. Wiley-Interscience. New York). These references, and all other references cited herein are hereby incorporated by reference in their entirety as if fully set forth.

However, recent research conducted with modem molecular methods which use the uniqueness of the DNA sequence of an organism (or group of organisms) has shown that *N. europaea* and its close relatives were below detection limits in freshwater aquaria environments (Hovanec, T. A. and E. F. DeLong. 1996. Comparative analysis of nitrifying bacteria associated with freshwater and marine aquaria. Appl. Environ. Microbiol. 62:2888-2896.). Other research has demonstrated that *N. europaea* is not the dominant AOB in wastewater treatment facilities (Juretschko, S. et. al. 1998. Combined molecular and conventional analyses of nitrifying bacterium diversity in activated sludge: *Nitrosococcus mobilis* and *Nitrospira*-like bacteria as dominant populations. Appl. Environ. Microbiol. 64:3042-3051).

Moreover, an environmental factor of particular import with aquaria environments and wastewater treatment is salinity, and, more specifically, the numerous physicochemical differences between freshwater and saltwater environments. The distinction among various AOBs in their ability to tolerate such dramatic changes in local environment is critical in the design of these systems and implementation of AOBs therein. As such, a demonstrated tolerance by a particular AOB to a saltwater environment may render that AOB suitable for use in particular aquaria and wastewater environments, and, moreover, a resilience to withstand the change between a freshwater and saltwater environment may have even broader implications.

Furthermore, the storage and transport of AOB is often limited to liquid and similar, potentially inconvenient media, owing, at least in part, to the inability of various strains of AOB to withstand a freeze-drying process. Such a process allows one to formulate a volume of AOB into a solid, freeze-dried powder or similar composition that may be tolerant of greater fluctuations in, e.g., temperature, and may be correspondingly more practical for purposes of shipping and handling in a commercialized product, or similar considerations, and for maintaining an extended shelf-life.

Thus, there exists a need in the art for the identification of AOBs, particularly those which are capable of tolerating a saltwater environment and/or both saltwater and freshwater environments. There is also a need in the art for AOBs that remain viable after being subjected to a freeze-drying process.

SUMMARY OF THE INVENTION

In an embodiment of the present invention, isolated bacteria or bacterial strains capable of oxidizing ammonia to nitrite are provided. In one embodiment, the 16S rDNA of the bacteria or bacterial strains have the nucleotide sequence of SEQ ID NO:1, SEQ ID NO:2, SEQ ID NO:3, SEQ ID NO:4, SEQ ID NO:18, SEQ ID NO:19 or SEQ ID NO:20. The nucleotide sequences described as SEQ ID NO:18, SEQ ID NO:19 and SEQ ID NO:20 are exemplary of *Nitrosomonas aestuarii*-like AOB. The *Nitrosospira*-like AOB represented by SEQ ID NO:1, SEQ ID NO:2 and SEQ ID NO:3 have been deposited with the American Type Culture Collection (ATCC) and have been assigned accession numbers PTA-1888, PTA-1887 and PTA-1885, respectively. The *Nitrosomonas*-like AOB represented by SEQ ID NO:4 has been deposited with the ATCC and has been assigned accession number PTA-1886. The *Nitrosomonas aestuarii*-like AOB represented by SEQ ID NO:18, SEQ ID NO:19 and SEQ ID NO:20 have been deposited with the ATCC and have been assigned accession number PTA-5423.

In various embodiments, the 16S rDNA of the bacteria or bacterial strains have the nucleotide sequence of SEQ ID NO:18, SEQ ID NO:19 or SEQ ID NO:20 (i.e., the *Nitrosomonas aestuarii*-like AOB), SEQ ID NO:1, SEQ ID NO:2, SEQ ID NO:3, SEQ ID NO:4 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:18, SEQ ID NO:19 or SEQ ID NO:20.

The present invention also includes nucleic acid sequences and bacteria with sequences which have the nucleotide sequence of SEQ ID NO:1, SEQ ID NO:2, SEQ ID NO:3, SEQ ID NO:4, SEQ ID NO:18, SEQ ID NO:19 or SEQ ID NO:20 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:18, SEQ ID NO:19 or SEQ ID NO:20.

For the purposes of this application, "96% similar" means that single base substitutions may occur in up to 4% of the bases, "97% similar" means that single base substitutions may occur in up to 3% of the bases, "98% similar" means that single base substitutions may occur in up to 2% of the bases and "99% similar" means that single base substitutions may occur in up to 1% of the bases.

DETAILED DESCRIPTION OF THE INVENTION

Figure 1:
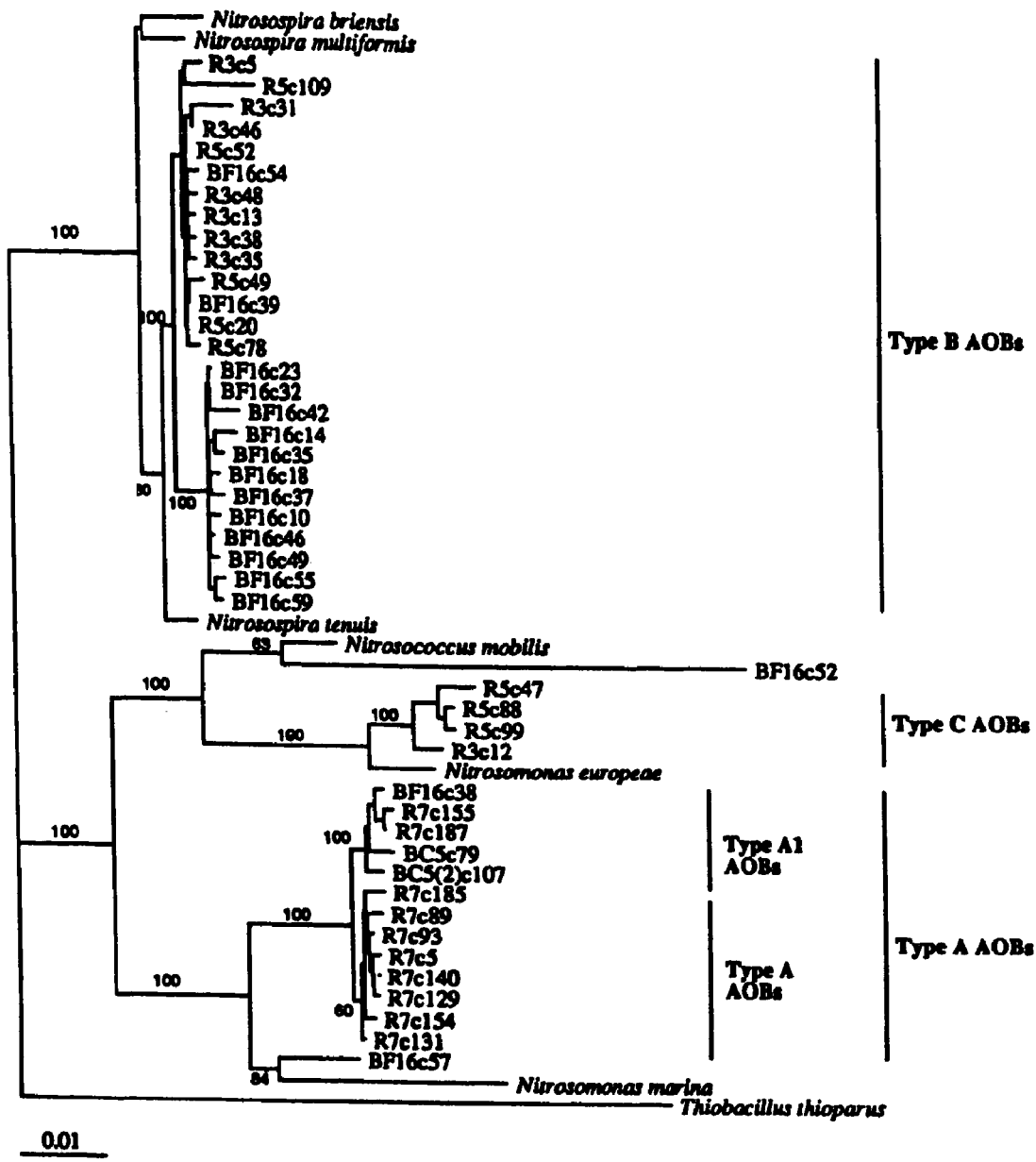
FIG. 1 illustrates the phylogenetic relationships of three bacterial strains (i.e., those represented by SEQ ID NO:1, SEQ ID NO:2 and SEQ ID NO:3) and one substrain (i.e., that strain represented by SEQ ID NO:4) inferred from comparative analysis of 16S rDNA sequences in accordance with an embodiment of the present invention. The tree is based on neighbor-joining distance analysis of sequences containing a minimum of 1430 nucleotides.

The present invention is based upon the discovery of novel bacterial strains which are capable of ammonia oxidation in freshwater and/or saltwater environments, and which can also survive and remain viable following a freeze-drying process.

The present invention provides an isolated bacterial strain or a biologically pure culture of a bacterial strain capable of oxidizing ammonia to nitrite, wherein the 16S rDNA of the bacterial strain includes the nucleotide sequence of SEQ ID NO:1, SEQ ID NO:2, SEQ ID NO:3 and SEQ ID NO:4, SEQ ID NO:18, SEQ ID NO:19 or SEQ ID NO: 22 as shown in Tables 1 through 7.

TABLE 1

The sequence for the AOB
Type A ammonia-oxidizing bacterium.
Represented by R7clone140. SEQ ID NO: 1.

ATTGAACGCTGGCGGCATGCTTTACACATGCAAGTCGAACGGCAGCACGG
ATGCTTGCATCTGGTGGCGAGTGGCGGACGGGTGAGTAATGCATCGGAAC
GTATCCAGAAGAGGGGGTAACGCATCGAAAGATGTGCTAATACCGCATA
TACTCTAAGGAGGAAAGCAGGGGATCGAAAGACCTTGCGCTTTTGGAGCG
GCCGATGTCTGATTAGCTAGTTGGTGGGGTAAAGGCCTACCAAGGCGACG
ATCAGTAGTTGGTCTGAGAGGACGACCAGCCACACTGGGACTGAGACACG
GCCCAGACTCCTACGGGAGGCAGCAGTGGGGAATTTTGGACAATGGGCGC
AAGCCTGATCCAGCAATGCCGCGTGAGTGAAGAAGGCCTTCGGGTTGTAA
AGCTCTTTCAGTCGAGAAGAAAAGGTTACGGTAAATAATCGTGACTCATG
ACGGTATCGACAGAAGAAGCACCGGCTAACTACGTGCCAGCAGCCGCGGT
AATACGTAGGGTGCAAGCGTTAATCGGAATTACTGGGCGTAAAGGGTGCG
CAGGCGGCTTTGTAAGTCAGATGTGAAATCCCCGGGCTTAACCTGGGAAT
TGCGTTTGAAACTACAAGGCTAGAGTGTGGCAGAGGGAGGTGGAATTCCA
TGTGTAGCAGTGAAATGCGTAGAGATATGGAAGAACATCGATGGCGAAGG
CAGCCTCCTGGGTTAACACTGACGCTCATGCACGAAAGCGTGGGGAGCAA
ACAGGATTAGATACCCTGGTAGTCCACGCCCTAAACGATGTCAACTAGTT
GTTGGGCCTTATTAGGCTTGGTAACGAAGCTAACGCGTGAAGTTGACCGC
CTGGGGAGTACGGTCGCAAGATTAAAACTCAAAGGAATTGACGGGGACCC
GCACAAGCGGTGGATTATGTGGATTAATTCGATGCAACGCGAAAAACCTT
ACCTACCCTTGACATGTAGCGAATTTTCTAGAGATAGATTAGTGCTTCGG
GAACGCTAACACAGGTGCTGCATGGCTGTCGTCAGCTCGTGTCGTGAGAT
GTTGGGTTAAGTCCCGCAACGAGCGCAACCCTTGTCATTAATTGCCATCA
TTTGGTTGGGCACTTTAATGAGACTGCCGGTGACAAACCGGAGGAAGGTG
GGGATGACGTCAAGTCCTCATGGCCCTTATGGGTAGGGCTTCACACGTAA
TACAATGGCGCGTACAGAGGGTTGCCAACCCGCGAGGGGAGCTAATCTC
AGAAAGCGCGTCGTAGTCCGGATCGGAGTCTGCAACTCGACTCCGTGAAG
TCGGAATCGCTAGTAATCGCGGATCAGCATGTCGCGGTGAATACGTTCCC
GGGTCTTGTACACACCGCCCGTCACACCATGGGAGTGGGTTTCACCAGAA
GCAGGTAGTCTAACCGTAAGGAGGGCGCTTGCCACGGTGAGATTCATGAC
TGGGGTG

TABLE 2

The sequence f r the AOB
Type A1 ammonia-oxidizing bacterium.
Represented by R7clone187. SEQ ID NO: 2.

ATTGAACGCTGGCGGCATGCTTTACACATGCAAGTCGAACGGCAGCACGG
ATGCTTGCATCTGGTGGCGAGTGGCGGACGGGTGAGTAATGCATCGGAAC
GTATCCAGAAGAGGGGGTAACGCATCGAAAGATGTGCTAATACCGCATA

TABLE 2-continued

The sequence f r the AOB
Type A1 ammonia-oxidizing bacterium.
Represented by R7clone187. SEQ ID NO: 2.

TACTCTAAGGAGGAAAGCAGGGGATCGAAAGACCTTGCGCTTTTGGAGCG
GCCGATGTCTGATTAGCTAGTTGGTGGGGTAAAGGCCTACCAAGGCGACG
ATCAGTAGTTGGTCTGAGAGGACGACCAGCCACACTGGGACTGAGACACG
GCCCAGACTCCTACGGGAGGCAGCAGTGGGGAATTTTGGACAATGGGCGC
AAGCCTGATCCAGCAATGCCGCGTGAGTGAAGAAGGCCTTCGGGTTGTAA
AGCTCTTTCAGTCGAGAAGAAAAGGTTACGGTAAATAATCGTGACCCATG
ACGGTATCGACAGAAGAAGCACCGGCTAACTACGTGCCAGCAGCCGCGGT
AATACGTAGGGTGCAAGCGTTAATCGGAATTACTGGGCGTAAAGGGTGCG
CAGGCGGCCTTGTAAGTCAGATGTGAAATCCCCGGGCTTAACCTGGGAAT
TGCGTTTGAAACTACAAAGCTAGAGTGTGGCAGAGGGAGGTGGAATTCCA
TGTGTAGCAGTGAAATGCGTAGAGATATGGAAGAACATCGATGGCGAAGG
CAGCCTCCTGGGTTAACACTGACGCTCATGCACGAAAGCGTGGGGAGCAA
ACAGGATTAGATACCCTGGTAGTCCACGCCCTAAACGATGTCAACTAGTT
GTTGGGCCTTATTAGGCTTGGTAACGAAGCTAACGCGTGAAGTTGACCGC
CTGGGGAGTACGGTCGCAAGATTAAAACTCAAAGGAATTGACGGGGACCC
GCACAAGCGGTGGATTATGTGGATTAATTCGATGCAACGCGAAAAACCTT
ACCTACCCTTGACATGTAGCGAATTTTCTAGAGATAGATTAGTGCTTCGG
GAACGCTAACACAGGTGCTGCATGGCTGTCGTCAGCTCGTGTCGTGAGAT
GTTGGGTTAAGTCCCGCAACGAGCGCAACCCTTGTCATTAATTGCCATCA
TTTGGTTGGGCACTTTAATGAGACTGCCGGTGACAAACCGGAGGAAGGTG
GGGATGACGTCAAGTCCTCATGGCCCTTATGGGTAGGGCTTCACACGTAA
TACAATGGCGCGTACAGAGGGTTGCCAACCCGCGAGGGGAGCTAATCTC
AGAAAGCGCGTCGTAGTCCGGATCGGAGTCTGCAACTCGACTCCGTGAAG
TCGGAATCGCTAGTAATCGCGGATCAGCATGTCGCGGTGAATACGTTCCC
GGGTCTTGTACACACCGCCCGTCACACCATGGGAGTGGGTTTCACCAGAA
GCAGGTAGTCTAACCGTAAGGAGGGCGCTTGCCACGGTGAGATTCATGAC
TGGGGTG

TABLE 3

The sequence for the AOB Type B ammonia-oxidizing bacterium.
Represented by R3clone5. SEQ ID NO:3.

ATTGAACGCTGGCGGCATGCTTTACACATGCAAGTCGAACGGCAGCACGGGG

GCAACCCTGGTGGCGAGTGGCGAACGGGTGAGTAATACATCGGAACGTATCT

TCGAGGGGGGATAACGCACCGAAAGGTGTGCTAATACCGCATAATCTCCAC

GGAGAAAAGCAGGGGATCGCAAGACCTTGCGCTCTTGGAGCGGCCGATGTCT

GATTAGCTAGTTGGTGAGGTAATGGCTTACCAAGGCGACGATCAGTAGCTGG

TCTGAGAGGACGACCAGCCACACTGGGACTGAGACACGGCCCAGACTCCTAC

GGGAGGCAGCAGTGGGGAATTTTGGACAATGGGGGAAACCCTGATCCAGCCA

TGCCGCGTGAGTGAAGAAGGCCTTCGGGTTGTAAAGCTCTTTCAGCCGGAAC

GAAACGGTCACGGCTAATACCCGTGACTACTGACGGTACCGGAAGAAGAAG

CACCGGCTAACTACGTGCCAGCAGCCGCGGTAATACGTAGGGTGCAAGCGTT

AATCGGAATTACTGGGCGTAAAGCGTGCGCAGGCGGTTTTGTAAGTCAGATG

TGAAAGCCCCGGGCTTAACCTGGGAACTGCGTTTGAAACTACAAGGCTAGAG

TGTGGCAGAGGGGGTGGAATTCCACGTGTAGCAGTGAAATGCGTAGAGATG

TGGAGGAACACCGATGGCGAAGGCAGCCCCCTGGGTTAACACCGACGCTCAG

GCACGAAAGCGTGGGGAGCAAACAGGATTAGATACCCTGGTAGTCCACGCCC

TAAACGATGTCAACTAGTTGTCGGGTCTTAACGGACTTGGTAACGCAGCTAA

CGCGTGAAGTTGGCCGCCTGGGGAGTACGGTCGCAAGATTAAAACTCAAAGG

AATTGACGGGGACCCGCACAAGCGGTGGATTATGTGGATTAATTCGATGCAA

CGCGAAAAACCTTACCTACCCTTGACATGTACCGAAGCCCGCCGAGAGGTGG

GTGTGCCCGAAAGGGAGCGGTAACACAGGTGCTGCATGGCTGTCGTCAGCTC

GTGTCGTGAGATGTTGGGTTAAGTCCCGCAACGAGCGCAACCCTTGTCATTA

ATTGCCATCATTCAGTTGGGCACTTTAATGAAACTGCCGGTGACAAACCGGA

GGAAGGTGGGGATGACGTCAAGTCCTCATGGCCCTTATGGGTAGGGCTTCAC

ACGTAATACAATGGCGCGTACAGAGGGTTGCCAACCCGCGAGGGGGAGCTAA

TCTCAGAAAGCGCGTCGTAGTCCGGATCGGAGTCTGCAACTCGACTCCGTGA

AGTCGGAATCGCTAGTAATCGCGGATCAGCATGTCGCGGTGAATACGTTCCC

GGGTCTTGTACACACCGCCCGTCACACCATGGGAGTGGGTTTCACCAGAAGC

AGGTAGTCTAACCGCAAGGAGGGCGCTTGCCACGGTGAGATTCATGACTGGG

GTG

TABLE 4

The sequence for the AOB Type C ammonia-oxidizing
bacterium. Represented by R5clone47. SEQ ID NO: 4.

ATTGAACGCTGGCGGCATGCTTTACACATGCAAGTCGAACGGCAGCGGGG

GCTTCGGCCTGCCGGCGAGTGGCGAACGGGTGAGTAATACATCGGAACGT

GTCCTTAAGTGGGGAATAACGCATCGAAAGATGTGCTAATACCGCATATC

TCTGAGGAGAAAAGCAGGGGATCGCAAGACCTTGCGCTAAAGGAGCGGCC

GATGTCTGATTAGCTAGTTGGTGGGGTAAAGGCTTACCAAGGCAACGATC

TABLE 4-continued

The sequence for the AOB Type C ammonia-oxidizing
bacterium. Represented by R5clone47. SEQ ID NO: 4.

AGTAGTTGGTCTGAGAGGACGACCAACCACACTGGGACTGAGACACGGCC

CAGACTCCTACGGGAGGCAGCAGTGGGGAATTTTGGACAATGGGCGAAAG

CCTGATCCAGCCATGCCGCGTGAGTGAAGAAGGCCTTCGGGTTGTAGAGC

TCTTTTAGTCAGAAAGAAAGAATCATGATGAATAATTATGATTTATGACG

TABLE 4-continued

The sequence for the AOB Type C ammonia-oxidizing bacterium. Represented by R5clone47. SEQ ID NO: 4.

GTACTGACAGAAAAAGCACCGGCTAACTACGTGCCAGCAGCCGCGGTAAT
ACGTAGGGTGCGAGCGTTAATCGGAATTACTGGGCGTAAAGGGTGCGCAG
GCGGTTTTGTAAGTCAGATGTGAAAGCCCCGGGCTTAACCTGGGAATTGC
GTTTGAAACTACAAGGCTAGAGTGCAGCAGAGGGGAGTGGAATTCCATGT
GTAGCAGTGAAATGCGTAGAGATGTGGAAGAACACCGATGGCGAAGGCAG
CTCCCTGGGTTGACACTGACGCTCATGCACGAAAGCGTGGGGAGCAAACA
GGATTAGATACCCTGGTAGTCCACGCCCTAAACGATGTCAACTGGTTGTC
GGATCTAATTAAGGATTTGGTAACGTAGCTAACGCGTGAAGTTGACCGCC
TGGGGAGTACGGTCGCAAGATTAAAACTCAAAGGAATTGACGGGGACCCG
CACAAGCGGTGGATTATGTGGATTAATTCGATGCAACGCGAAAAACCTTA
CCTACCCTTGACATGCTTGGAATCTAGTGGAGACATAAGAGTGCCCGAAA
GGGAGCCAAGCACAGGTGCTGCATGGCTGTCGTCAGCTCGTGTCGTGAG
ATGTTGGGTTAAGTCCCGCAACGAGCGCAACCCTTGTCACTAATTGCTAT
CATTCTAAATGAGCACTTTAGTGAGACTGCCGGTGACAAACCGGAGGAAG
GTGGGGATGACGTCAAGTCCTCATGGCCCTTATGGGTAGGGCTTCACACG
TAATACAATGGCGTGTACAGAGGGTTGCCAACCCGCGAGGGGAGCCAAT
CTCAGAAAGCACGTCGTAGTCCGGATCGGAGTCTGCAACTCGACTCCGTG
AAGTCGGAATCGCTAGTAATCGCGGATCAGCATGCCGCGGTGAATACGTT
CCCGGGTCTTGTACACACCGCCCGTCACACCATGGGAGTGGTTTTCACCA
GAAGCAGGTAGTTTAACCGTAAGGAGGACGCTTGCCACGGTGGGGGTCAT
GACTGGGGTG

TABLE 5

The sequence for Nitrosomonas aestuarii-like AOB represented by P4clone42. SEQ ID NO: 18.

TTGATCATGGCTCAGATTGAACGCTGGCGGCATGCTTTACACATGCAAGT
CGAACGGCAGCACGGGTGCTTGCACCTGGTGGCGAGTGGCGGACGGGTGA
GTAATGCATCGGAACGTGTCCAGAAGTGGGGGATAACGCATCGAAAGATG
TGCTAATACCGCATATTCTCTACGGAGGAAAGCAGGGGATCGAAAGACCT
TGTGCTTTTGGAGCGGCCGATGCCTGATTAGCTAGTTGGTGGGGTAAAGG
CCTACCAAGGCAACGATCAGTAGTTGGTCTGAGAGGACGACCAGCCACAC
TGGGACTGAGACACGGCCCAGACTCCTACGGGAGGCAGCAGTGGGGAATT
TTGGACAATGGGCGAAAGCCTGATCCAGCAATGCCGCGTGAGTGAAGAAG
GCTTCGGGTTGTAAAGCTCTTTCAGTCGAGAAGAAAAGGTTGTGACTAAT
AATCACAACTTATGACGGTACCGACAGAAGAAGCACCGGCTAACTACGTG
CCAGCAGCCGCGGTAATACGTAGGGTGCAAGCGTTAATCGGAATTACTGG
GCGTAAAGGGTGCGCAGGCGGCTTTGTAAGTCAGATGTGAAATCCCCGGG
CTTAACCTGGGAATTGCGTTTGAAACTACAAAGCTAGAGTGTAGCAGAGG

TABLE 5-continued

The sequence for Nitrosomonas aestuarii-like AOB represented by P4clone42. SEQ ID NO: 18.

GGGGTGGAATTCCATGTGTAGCAGTGAAATGCGTAGAGATATGGAAGAAC
ATCGATGGCGAAGGCAGCCCCCTGGGTTAACACTGACGCTCATGCACGAA
AGCGTGGGGAGCAAACAGGATTAGATACCCTGGTAGTCCACGCCCTAAAC
GATGTCAACTAGTTGTTGGGCCTTACTAGGCTTGGTAACGTAGCTAACGC
GTGAAGTTGACCGCCTGGGGAGTACGGTCGCAGGATTAAAACTCAAAGGA
ATTGACGGGGACCCGCACAAGCGGTGGATTATGTGGATTAATTCGATGCA
ACGCGAAAAACCTTACCTACCCTTGACATGTAGCGAATATTTTAGAGATA
AATAGTGCCTTCGGGAACGCTAACACAGGTGCTGCATGGCTGTCGTCAGC
TCGTGTCGTGAGATGTTGGGTTAAGTCCCGCAACGAGCGCAACCCTTGTC
ATTAATTGCCATCATTTAGTTGGGCACTTTAATGAGACTGCCGGTGACAA
ACCGGAGGAAGGTGGGGATGACGTCAAGTCCTCATGGCCCTTATGGGTAG
GGCTTCACACGTAATACAATGGCGCGTACAGAGGGTTGCCAACCCGCGAG
GGGGAGCTAATCTCAGAAAGCGCGTCGTAGTCCGGATCGGAGTCTGCAAC
TCGACTCCGTGAAGTCGGAATCGCTAGTAATCGCGGATCAGCATGTCGCG
GTGAATACGTTCCCGGGTCTTGTACACACCGCCCGTCACACCATGGGAGT
GGGTTTCACCAGAAGCAGATAGTCTAACCGTAAGAGGGCGTTTGCCACGG
CGAGATTCATGACTGG

TABLE 6

The sequence for Nitrosomonas aestuarii-like AOB represented by P4clone31. SEQ ID NO: 19.

AGTTTGATCATGGCTCAGATTGAACGCTGGCGGCATGCTTTACACATGCA
AGTCGAACGGCAGCACGGGTGCTTGCACCTGGTGGCGAGTGGCGGACGGG
TGAGTAATGCATCGGAACGTGTCCGGAAGTGGGGGATAACGCATCGAAAG
ATGTGCTAATACCGCATATTCTCTACGGAGGAAAGCAGGGGATCGAAAGA
CCTTGTGCTTTTGGAGCGGCCGATGCCTGATTAGCTAGTTGGTGGGGTAA
AGGCCTACCAAGGCAACGATCAGTAGTTGGTCTGAGAGGACGACCAGCCA
CACTGGGACTGAGACACGGCCCAGACTCCTACGGGAGGCAGCAGTGGGGA
ATTTTGGACAACGGGCGAAAGCCTGATCCAGCAATGCCGCGTGAGTGAAG
AAGGCCTTCGGGTTGTAAAGCTCTTTCAGTCGAGAAGAAAAGGTTGTGAC
TAATAATCACAACTTATGACGGTACCGACAGAAGAAGCACCGGCTAACTA
CGTGCCAGCAGCCGCGGTAATACGTAGGGTGCAAGCGTTAATCGGAATTA
CTGGGCGTAAAGGGTGCGCAGGCGGCTTTGTAAGTCAGATGTGAAATCCC
CGGGCTTAACCTGGGAATTGCGTTTGAAACTACAAAGCTAGAGTGTAGCA
GAGGGGGTGGAATTCCATGTGTAGCAGTGAAATGCGTAGAGATATGGAA
GAACATCGATGGCGAAGGCAGCCCCCTGGGTTAACACTGACGCTCATGCA
CGAAAGCGTGGGGAGCAAACAGGATTAGATACCCTGGTAGTCCACGCCCT
AAACGATGTCAACTAGTTGTTGGGCCTTACTAGGCTTGGTAACGTAGCTA

TABLE 6-continued

The sequence for *Nitrosomonas aestuarii*-like AOB represented by P4clone31. SEQ ID NO: 19.

ACGCGTGAAGTTGACCGCCTGGGGAGTACGGTCGCAAGATTAAAACTCAA

AGGAATTGACGGGGACCCGCACAAGCGGTGGATTATGTGGATTAATTCGA

TGCAACGCGAAAAACCTTACCTACCCTTGACATGTAGCGAATATTTTAGA

GATAAAATAGTGCCTTCGGGAACGCTAACACAGGTGCTGCATGGCTGTCG

TCAGCTCGTGTCGTGAGATGTTGGGTTAAGTCCCGCAACGAGCGCAACCC

TTGTCATTAATTGCCATCATTTAGTTGGGCACTTTAATGAGACTGCCGGT

GACAAACCGGAGGAAGGTGGGGATGACGTCAAGTCCTCATGGCCCTTATG

GGTAGGGCTTCACACGTAATACAATGGCGCGTACAGAGGGTTGCCAACCC

GCGAGGGGGAGCTAATCTCAGAAAGCGCGTCGTAGTCCGGATCGGAGTTA

GCAACTCGACTCCGTGAAGTCGGAATCGCTAGTAATCGCGGATCAGCATG

TCGCGGTGAATACGTTCCCGGGCCTTGTACACACCGCCCGTCACACCATG

GAAGTTGGCTGCACCAGAAGTAGGTTGTCTAACCCTCGGGAGGACGCTTA

CCACGGTGTGGTCAATGACTTGGGGTGAAGTCGTAACAAGGTAA

TABLE 7

The sequence for *Nitrosomonas aestuarii*-like AOB represented by BF16clone57. SEQ ID NO: 20.

GTTTGATCATGGCTCAGATTGAACGCTGGCGGCATGCTTTACACATGCAA

GTCGAACGGCAGCACGGGTGCTTGCACCTGGTGGCGAGTGGCGGACGGGT

GAGTAATGCATCGGAACGTGTCCAGAAGTGGGGGATAACGCATCGAAAGA

TGTGCTAATACCGCATATTCTCTACGGAGGAAAGCAGGGGATCGAAAGAC

CTTGTGCTTTTGGAGCGGCCGATGCCTGATTAGCTAGTTGGTGGGGTAAA

GGCCTACCAAGGCAACGATCAGTAGTTGGTCTGAGAGGACGACCAGCCAC

ACTGGGACTGAGACACGGCCCAGACTCCTACGGGAGGCAGCAGTGGGGAA

TTTTGGACAATGGGCGAAAGCCTGATCCAGCAATGCCGCGTGAGTGAAGA

AGGCCTTCGGGTTGTAAAGCTCTTTCAGTCGAGAAGAAAAGGTTGTGACT

AATAATCACAACTTATGACGGTACCGACAGAAGAAGCACCGGCTAACTAC

GTGCCAGCAGCCGCGGTAATACGTAGGGTGCAAGCGTTAATCGGAATTAC

TGGGCGTAAAGGGTGCGCAGGCGGCTTTGTAAGTCAGATGTGAAATCCCC

GGGCTTAACCTGGGAATTGCGTTTGAAACTACAAAGCTAGAGTGTAGCAG

AGGGGGGTGGAATTCCATGTGTAGCAGTGAAATGCGTAGAGATATGGAAG

AACATCGATGGCGAAGGCAGCCCCCTGGGTTAACACTGACGCTCATGCAC

GAAAGCGTGGGGAGCAAACAGGATTAGATACCCTGGTAGTCCACGCCCTA

AACGATGTCAACTAGTTGTTGGGCCTTACTAGGCTTGGTAACGTAGCTAA

CGCGTGAAGTTGACCGCCTGGGGAGTACGGTCGCAAGATTAAAACTCAA

GGAATTGACGGGGACCCGCACAAGCGGTGGATTATGTGGATTAATTCGAT

GCAACGCGAAAAACCTTACCTACCCTTGACATGTAGCGAATATTTTAGAG

ATAAAATAGTGCCTTCGGGAACGCTAACACAGGTGCTGCATGGCTGTCGT

TABLE 7-continued

The sequence for *Nitrosomonas aestuarii*-like AOB represented by BF16clone57. SEQ ID NO: 20.

CAGCTCGTGTCGTGAGATGTTGGGTTAAGTCCCGCAACGAGCGCAACCCT

TGTCATTAATTGCCATCATTTAGTTGGGCACTTTAATGAGACTGCCGGTG

ACAAACCGGAGGAAGGTGGGGATGACGTCAAGTCCTCATGGCCCTTATGG

GTAGGGCTTCACACGTAATACAATGGCGCGTACAGAGGGTTGCCAACCCG

CGAGGGGGAGCTAATCTCAGAAAGCGCGTCGTAGTCCGGATCGGAGTCTG

CAACTCGACTCCGTGAAGTCGGAATCGCTAGTAATCGCGGATCAGCATGT

CGCGGTGAATACGTTCCCGGGTCTTGTACACACCGCCCGTCACACCATGG

GAGTGGGTTTCACCAGAAGCAGATAGTCTAACCGTAAGGAGGGCGTTTGC

CACGGTGAGATTCATGACTGGGGTGAAGTCGTAACAATTTA

For the purposes of the present invention, an isolated bacterial strain is one that has undergone some degree of purification from its natural environment. A culture of a bacterium is considered to be biologically pure if at least 20% of the bacteria are from one bacterial strain. However, it is preferable if the culture is at least 33% pure, more preferable if the culture is at least 45% pure and most preferable if the culture is at least 90% pure.

The bacterial strains of the present invention may also be combined with each other, other species of bacteria, nutrients and/or other components to provide a composition for maintaining or purifying water-containing media. It may be desirable, for example, to combine the bacteria of the present invention with bacteria capable of removing other pollutants or undesirable compounds from water-containing media. Examples of such bacteria include nitrite-oxidizing bacteria (chemolithoautotrophic bacteria which oxidize nitrite to nitrate), heterotrophic bacteria (which mineralize organic material into ammonia and other substances) and other bacteria which will be known to those of skill in the art. Nitrite-oxidizing bacteria are known from the Nitrospira phylum of bacteria, and the alpha, gamma and delta subdivisions of the Proteobacteria. Examples include species of the genera *Nitrospira*, *Nitrospina* and *Nitrobacter*. Nitrate-reducing bacteria are known from the genera *Azoarcus*, *Pseudomonas* and *Alcaligenes*. Heterotrophic bacteria are known from the genera *Bacillus, Planctomyces, Pseudomonas* and *Alcaligenes*. Such are available from known sources (e.g., American Type Culture Collection, 10801 University Blvd., Manassas Va. 20100, USA) or may be isolated directly from aquaria biofilters.

For example, the bacterial strains of the present invention may be combined with nitrite-oxidizing bacteria such that ammonia present in the water system would be oxidized to nitrite and the nitrite oxidized to nitrate. Another example would be to combine the bacterial strain of the present invention with aerobic or anaerobic denitrifying bacteria. In this case, the nitrate which is produced by the interaction of the bacterial strains of the present invention with nitrite-oxidizing bacteria would be reduced to dinitrogen or other nitrogen based products. A third example would be to combine the bacterial strain of the present invention with heterotrophic bacteria which mineralize organic matter into simpler inorganic substances which, subsequently, can be utilized as substrates by the bacterial strains of the present invention.

The present invention also provides a mixture comprising a concentrated bacterial strain capable of oxidizing ammonia to nitrite, wherein the 16S rDNA of the bacteria has a nucleotide sequence of SEQ ID NO:1, SEQ ID NO:2, SEQ ID NO:3, SEQ ID NO:4, SEQ ID NO:18, SEQ ID NO:19 or SEQ ID NO:20 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:18, SEQ ID NO:19 or SEQ ID NO:20. According to this embodiment of the invention, the bacterial strain is considered to be concentrated if the bacterial strain occurs in a concentration which is higher than its concentration occurred in nature. In general, the concentration of the bacterial strain will be at least 20% of the total cells in the sample as determined by standard techniques such as molecular probing using fluorescent in situ hybridization (FISH) techniques, which will be known to those skilled in the art, using appropriate controls and enumeration methods. More preferably, the concentration of the bacterial strain would be 33% or greater of the total cells, even more preferably 45%, and most preferably 90% or greater of the total cells. However, it may be preferable to have more than one of the bacteria which have a nucleotide sequence of SEQ ID NO:1, SEQ ID NO:2, SEQ ID NO:3, SEQ ID NO:4, SEQ ID NO:18, SEQ ID NO:19 or SEQ ID NO:20 in the mixture. In this case, the percentages stated above relate to percentage of total AOBs in the mixture with the understanding that the balance of cell population might be comprised of nitrite-oxidizing bacteria or other types of bacteria.

In particular, while not wishing to be bound by any theory, of the various bacterial strains described in accordance with the present invention, those strains represented by SEQ ID NO:18, SEQ ID NO:19 and SEQ ID NO:20 are believed to be especially tolerant of saltwater environments; although these strains may be utilized in freshwater environments, as well, and are believed to function effectively therein. Bacterial strains and mixtures incorporating strains other than those strains represented by SEQ ID NO:18, SEQ ID NO:19 and SEQ ID NO:20 may also tolerate saltwater environments to an appreciable degree, yet in a preferred embodiment of the present invention, it is those strains represented by SEQ ID NO:18, SEQ ID NO:19 or SEQ ID NO:20 that are included in a saltwater environment to oxidize ammonia to nitrite.

Furthermore, any of the bacterial strains of the present invention may be freeze-dried, and are believed to be particularly tolerant of the freeze-drying process, as evidenced by their ability to remain viable after such a process, and to oxidize ammonia to nitrite following such a process. Thus, in a further embodiment of the present invention, any of the bacterial strains described herein may be freeze-dried and thereafter used to oxidize ammonia to nitrite.

It is understood that the bacterial strains and the mixtures of the present invention can be in the form of powder, liquid, a frozen form, a freeze-dried form or any other suitable form, which may be readily recognized by one of skill in the art. These are commonly referred to as "commercial additives," and may include, but are in no way limited to:

(1) a liquid form, wherein one or more strains are in a liquid solution containing inorganic salts or organic compounds such that the viability of the cells is not destroyed during the course of storage;

(2) a frozen form, wherein one or more of the strains are in a liquid mixture as above, optionally including cryoprotectant compounds to prevent cell lysis, which is frozen and stored at a temperature at or below 32° F.; and (3) a powder form, which has been produced by freeze-drying or other means, wherein the dehydrated form of one or more of the strains or mixture can be stored at normal room temperature without loss of viability.

Obtaining a proper form of the bacterial strain and the mixture of the present invention is well within the skill in the art in view of the instant disclosure. It is also understood that the bacterial strains and the mixture of the present invention can be used alone, or in combination with other components. Examples of such components include, but are not limited to, nitrite-oxidizing bacteria, heterotrophic nitrite-oxidizing bacteria, heterotrophic ammonia-oxidizing bacteria and the like. All of the forms of the biologically pure bacterial strain may also contain nutrients, amino acids, vitamins and other compounds which serve to preserve and promote the growth of the bacterial strain. The bacterial strains and the mixtures and compositions of the present invention can be used in freshwater aquaria, seawater aquaria and wastewater to alleviate the accumulation of ammonia. They can also be used in a bioremediation process to reduce the level of pollution caused by the ammonia. A bioremediation process, also called bioaugmentation, includes, but is not limited to, the supplemental addition of microorganisms to a system (e.g. a site where biological or chemical contamination has occurred) for the purposes of promoting or establishing biological and/or chemical processes that result in the change of one or more forms of chemical compounds present in the original system.

Accordingly, one aspect of the present invention provides a method of alleviating the accumulation of ammonia in a medium. The method includes a step of placing into the medium a sufficient amount of a bacterial strain capable of oxidizing ammonia to nitrite to alleviate the accumulation of ammonia in the medium, wherein the 16S rDNA of the bacteria strain has a nucleotide sequence of SEQ ID NO:1, SEQ ID NO:2, SEQ ID NO:3, SEQ ID NO:4, SEQ ID NO:18, SEQ ID NO:19 or SEQ ID NO:20 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:18, SEQ ID NO:19 or SEQ ID NO:20. The amount of the bacterial strain(s) is sufficient if the added bacteria can alleviate or prevent the accumulation of ammonia in the medium. In general, the addition of one or more of the bacterial strains of the invention to a freshwater or saltwater aquarium is expected to reduce the maximum ammonia concentration by at least 50% over the level which would be attained in the absence of the bacterial strain(s).

It will be appreciated that the actual levels achieved in a given setting will be a function of the size and contents of the systems (i.e., the number of fish, plants, etc.). In a newly set-up 37 liter aquarium with ten fish, the ammonia concentration may reach 7 mg/L or higher without addition of the bacterial strain, whereas the maximum level can be reduced to about 2 mg/L by addition of the bacterial strain. In general, the maximum ammonia concentration would not be expected to exceed 3 mg/L if the bacterial strain of the invention is added to such a system. When the system reaches a steady state, the ammonia levels drop back to below 0.5 mg/L, a process which occurs more rapidly when the bacterial strain of the invention is present.

In one embodiment of the present invention, the bacterial strains of the present invention are placed directly into a medium such as, but not limited to, freshwater aquaria, seawater aquaria and wastewater. In another embodiment of the present invention, the bacteria may be grown on a rotating biological contactor and then placed in the medium. In a different embodiment, the bacteria of the present invention can be placed on a biofilter unit contained in the medium. In another embodiment the bacteria of the present invention may be immobilized in an immobilizing polymer, such as, but not limited to, acrylamide, alginate or carrageenan. This bacterial-laced polymer material may then be placed in a filter or may itself be placed in the filter stream of a suitable facility.

As used herein, the term "aquarium" is intended to mean a container which may be made of, in combination or in its entirety, but not limited to, glass, plastic, or wood that holds water and in which living aquatic organisms (such as fish, plants, bacteria and invertebrates) are placed, and the contents thereof. An aquarium may be for the purposes of displaying aquatic organisms, for their short or long-term holding, for scientific study, for transportation and other purposes. A freshwater aquarium is generally an aquarium in which the liquid medium has a salinity of less than 15 parts per thousand. A saltwater aquarium is generally an aquarium in which the liquid medium has a salinity of more than 15 parts per thousand. The term "aquarium water" is used to refer to the medium which is contained within the aquarium, and its associated filter systems, in which the aquatic organisms reside. Aquarium water may contain a wide range of inorganic or organic chemical substances and, therefore, may have a wide range of parameters such as concentration of salts, pH, total dissolved solids and temperature, to name a few.

As used herein, "wastewater" generally refers to a liquid medium which is the product of an industrial or human process. It may require treatment by one or more filtration methods to render it less harmful to the environment such that it conforms to discharge standards as determined by a governmental agency. Wastewater may also be recycled such that it is not discharged to the environment.

As used herein, a "biological filter," also called a "biofilter," generally refers to a filter type whose purpose is to promote the growth of microorganisms, or to provide a substrate for the attachment and growth of microorganisms. A biofilter may be part of an aquarium filtration system or a wastewater filtration system. As used herein, the term "rotating biological contactor" generally refers to a type of biofilter which rotates in the water or medium. It may be completely or partially submerged in the water or medium. Persons skilled in the art will recognize rotating biological contactors as embodied in U.S. Pat. Nos. 2,085,217; 2,172,067; 5,423,978; 5,419,831; 5,679,253; 5,779,885 and all continuations, improvements and foreign counterparts; each of which is incorporated herein by reference as if fully set forth.

As used herein, "filter floss" refers to irregularly shaped natural or synthetic multi-stranded material which may serve as a biofilter, a mechanical filter or a combination of these.

As used herein, "aquarium gravel" refers to a substrate commonly placed inside, on the bottom, of an aquarium. It may be composed of irregular or regular shaped pieces of rock, coral, plastic or other material. It may serve as a biofilter, a mechanical filter, for decorative purposes or a combination of these.

As used herein, the term "filter sponge" refers to a natural or synthetic material which when used in an aquarium or as part of an aquarium filtration system may serve as a mechanical filter, a biofilter or both.

As used herein, "plastic filter media" refers to a man-made material which serves as a biofilter, a mechanical filter or both. It may be plastic molded or injected molded.

In another embodiment, nucleic acid sequences and bacteria with sequences which have the nucleotide sequence of SEQ ID NO:1, SEQ ID NO:2, SEQ ID NO:3, SEQ ID NO:4, SEQ ID NO:18, SEQ ID NO:19 or SEQ ID NO:20 or a variant thereof which is at least 96% similar, at least 97% similar, at least 98% similar or at least 99% similar to SEQ ID NO:1, SEQ ID NO:2, SEQ ID NO:3, SEQ ID NO:4, SEQ ID NO:18, SEQ ID NO:19 or SEQ ID NO:20 are also provided.

In another embodiment, oligonucleotide probes are provided that may be used to detect the bacteria and nucleic acid sequences of the present invention. The oligonucleotide probes are represented by SEQ ID NO:5, SEQ ID NO:8 and SEQ ID NO:21. A sequence that is at least 96% similar over the entire length of any of the aforementioned probes may also be used to detect the bacteria of the present invention. These probes are further described in the ensuing examples.

In another embodiment, PCR primers are provided that may be used to detect the bacteria and nucleic acid sequences of the present invention. The PCR primer pairs are represented by SEQ ID NO:6 and SEQ ID NO:7, SEQ ID NO:9 and SEQ ID NO:10, SEQ ID NO:11 and SEQ ID NO:12 and SEQ ID NO:22 and SEQ ID NO:23. A sequence that is at least 96% similar over the entire length of any of the aforementioned PCR primers may also be used to detect the bacteria of the present invention. These PCR primers are further described in the ensuing examples.

It would be readily apparent to one skilled in the art that variants of the aforementioned oligonucleotide probes and PCR primers that still may be used to detect the bacteria and nucleic acid sequences of the present invention are within the scope of the present invention. For example, a variant of any of the oligonucleotide probes or primers that differs from SEQ ID NO:5, SEQ ID NO:8, SEQ ID NO:21, SEQ ID NO:6, SEQ ID NO:7, SEQ ID NO:9, SEQ ID NO:10, SEQ ID NO:11, SEQ ID NO:12, SEQ ID NO:22 or SEQ ID NO:23 due to one or more nucleotide additions, deletions or substitutions, but still may be used to detect the bacteria and nucleic acid sequences of the present invention, is encompassed by the present invention.

The present invention includes isolated bacteria, isolated bacterial strains, bacterial cultures and nucleotide sequences comprising the sequences identified herein as SEQ ID NO:1, SEQ ID NO:2, SEQ ID NO:3, SEQ ID NO:4, SEQ ID NO:18, SEQ ID NO:19 and SEQ ID NO:20, or variants of those sequences. Particularly preferred variants are those in which there is a high degree of similarity to SEQ ID NO:1, SEQ ID NO:2, SEQ ID NO:3, SEQ ID NO:4, SEQ ID NO:18, SEQ ID NO:19 or SEQ ID NO:20. The present invention includes variants that are at least 96% similar, at least 97% similar, at least 98% similar or at least 99% similar to SEQ ID NO:1, SEQ ID NO:2, SEQ ID NO:3, SEQ ID NO:4, SEQ ID NO:18, SEQ ID NO:19 or SEQ ID NO:20. It is appreciated in the art that disclosures teaching those skilled in the art how to make and use a reference sequence (such as SEQ ID NO:1, SEQ ID NO:2, SEQ ID NO:3, SEQ ID NO:4, SEQ ID NO:18, SEQ ID NO:19 or SEQ ID NO:20) will also be sufficient to teach such an individual to make and use the described variants.

Three commonly-assigned patents describing nitrite-oxidizing bacteria, methods of using the bacteria and methods of detecting the bacteria issued in the United States (see U.S. Pat. Nos. 6,207,440, 6,265,206 and 6,268,154). All three patents describe a nucleotide sequence and any variants that have greater than 96.1% homology to that sequence. The issuance of these patents demonstrates that specifications setting forth particular sequences and describing particular variants enable one skilled in the art to make and use the sequence and its described variants. In addition, it is common in the art that patents disclosing nucleotide sequences also disclose and claim variants of those sequences (see, e.g. U.S. Pat. Nos. 6,465,621, 6,509,170 and 6,573,066).

Variants of particular nucleotide sequences may be naturally-occurring polymorphisms or synthetic sequence alterations (see, e.g., U.S. Pat. No. 6,485,938). A great diversity of modifications to nucleotide sequences, both natural and synthetic, are common and well known in the art, along with methods for making the synthetic variants (see, e.g. U.S. Pat. Nos. 6,448,044 and 6,509,170). Methods for comparing the similarity of two or more nucleotide sequences are well known in the art. Similar sequences are often identified using computer programs such as BESTFIT and BLAST (see, e.g., U.S. Pat. No. 6,461,836). Further, hybridization may be used to detect the similarity between variant sequences and a reference sequence (see, e.g., U.S. Pat. No. 6,573,066). Thus, one skilled in the art would be able to easily synthesize and identify nucleotide sequences that are variants of a reference sequence by using known techniques. Therefore, a specification that describes a nucleotide sequence and its variants allows one skilled in the art to make and use that sequence and its variants.

EXAMPLES

A series of assays and experiments were conducted to isolate, identify and show the efficacy of the bacterial strains reported herein. They involved a variety of bacterial culturing techniques, molecular biological analyses of DNA extracted from samples of the cultures, molecular biological analysis of the bacterial strains, and the application of concentrated cultures of the bacterial strains to aquaria to measure their ability to control ammonia concentrations.

Example 1

Bacteria Culturing

Bacterial culturing vessels (termed reactors) were constructed and seeded with bacterial biomass gathered from operating aquaria. Each reactor received 4.95 L of a mineral salt solution (made up in distilled water) containing 50 g $KH_2PO_4$, 50 g $K_2HPO_4$, 18.75 g $MgSO_4.7H_2O$, 1.25 g $CaCl_2.2H_2O$ and 1 g $FeSO_4.7H_2O$. Air was provided such that the dissolved oxygen was equal to or greater than 7.5 mg/L, stirring was provided, and the reactors were kept in a darkened cabinet at approximately 28° C.

For the isolation and culturing of strains of AOB of the present invention in saltwater environments, synthetic seasalts (INSTANT OCEAN, Aquarium Systems Inc., Mentor, Ohio) were added to reach a salt concentration of between 30 and 33 ppt.

The ammonia and nitrite concentrations were measured daily using flow injection analysis (FIA, Tecator FIAStar 5010 system) while pH was determined with an electrode (Denver Instruments Model 225 pH/ISE meter and associated pH/ATC electrode). Nitrate and conductivity were measured periodically and the data were used to determine when water changes were required. Bacterial biomass was retained in the reactors during water changes because the biomass is very floccular in nature. Thus prior to decanting 50% of the reactor's volume through the appropriate sampling port, the biomass was settled by turning off both the air and the stirring mechanism for one hour. Additionally, reactors were periodically scrubbed to remove the biomass from the surfaces and thereby return the biomass to suspension. Microbiological samples were taken routinely for DNA extraction (for PCR) and cell fixation (for FISH) for further analysis.

Example 2

Nucleic Acid Sampling and Extraction

For DNA extraction, samples of appropriate biological filtration media were taken and resuspended in cell lysis buffer (40 mM EDTA. 50 mM Tris-HCl, pH 8.3). Samples were stored at −20° C. or −74° C. until extraction. For processing, lysozyme was added to the samples to a final concentration of 10 mg/ml. After incubation at 37° C. for 90 minutes, 20% sodium dodecyl sulfate (SDS) was added to a final concentration of 1%. Then the samples were subjected to four freeze/thaw cycles followed by the addition of proteinase K (stock concentration, 10 mg/ml) to a final concentration of 2 mg/ml and incubated at 70° C. for 35 minutes. In some cases, additional proteinase K and SDS were added and the sample was incubated at 55° C. for another 30 minutes.

After cell lysis, DNA was extracted using Easy DNA extraction kit (Qiagen Inc., Santa Clarita, Calif.; hereinafter "Qiagen"). DNA was eluted to a 50 µl volume and quantified by Hoechst type 33258 dye binding and fluorometry (DynaQuant 200, Hoefer Pharmacia Biotech Inc., San Francisco, Calif.).

Example 3

Clone Libraries of PCR Amplified rRNA Genes

Clone libraries were derived from DNA extracts from biomass samples taken from reactors and aquaria. Bacterial ribosomal RNA gene fragments from bacteria represented by the sequences SEQ ID NO:1, SEQ ID NO:2, SEQ ID NO:3, SEQ ID NO:4, SEQ ID NO:18 and SEQ ID NO:20 were amplified with the primers S-D-Bact-0011-a-S-17 (8f; GTT TGA TCC TGG CTC AG) (SEQ ID NO:13) and 1492r (eubacterial; GGT TAC CTT GTT ACG ACT T) (SEQ ID NO:14). PCR conditions, cycle parameters, and reaction components were as previously described (DeLong, E. F. 1992. Archaea in coastal marine environments. Proc. Natl. Acad. Sci. USA 89: 5685-5689.) PCR products were evaluated by agarose gel electrophoresis. PCR fragments were cloned with a TA Cloning kit (Invitrogen, Carlsbad, Calif.), as described in the manufacturer's directions, after rinsing with TE buffer and concentrating to 30 µl with a CENTRICON concentrator (Amicon, Inc. Beverly, Mass.).

Example 4

Sequencing and Phylogenetic Analysis

The 16S rDNA insert from each clone that comprised the clone library were screened by restriction enzyme analysis (REA) using the restriction enzyme Hae III in order to ensure that the 16S rDNA insert was amplifiable and determine whether the 16S rDNA possessed a unique REA pattern when digested with the Hae III enzyme. If a clone was amplifiable and possessed a unique REA pattern, then the clone's plasmid containing the 16S rDNA insert of interest was partially sequenced. The amplified PCR 16S rDNA template of each clone selected for sequencing was cleaned using the PCR Purification Kit Catalog No. 28142 (Qiagen). Sequencing was performed using a LiCor 4000L automated DNA sequencer on template cycle-sequenced with fluorescently labeled primers and SEQUITHERM EXCEL II DNA Sequencing kits (Epicenter Technologies, Madison, Wis.).

Up to two or three clones of the same REA pattern were partially sequenced to ensure that they were identical. Many clones were fully sequenced and phylogenetically analyzed by PAUP (Phylogenetic Analysis Using Parsimony ver 4.0b2a, D. L. Swofford) (bootstrap values and distance analysis), ARB (A Software Environment for Sequence Date, W. Ludwig and O. Strunk) (phylogenetic tree) and Phylip (Phylogeny Inference Package J. Felsentein) (similarity matrix). Primers and probes for the clone of interest from the clone libraries were developed using ARB probe design and probe match programs as well as after manual alignment. Primers and probes were double checked with BLAST (S. F. Altschul et al. 1990. Basic local alignment tool. J. Mol. Biol. 215:403-410). The specificity of the primers was determined by using them on DNA extracted from clones and pure cultures of known bacteria. The specificity of the probes was tested using pure cultures of known bacteria and samples from the reactors.

Example 5

DGGE Analysis and Profiling

For general eubacterial DGGE analysis, rDNA fragments were amplified using the forward 358f (eubacterial; CCT ACG GGA GGC AGC AG) (SEQ ID No:15) with a 40-bp GC-clamp on the 5' end as described by Murray et al. (A. Murray et al. 1996. Phylogenetic compositions of bacterioplankton from two California estuaries compared by denaturing gradient gel electrophoresis of 16S rDNA fragments. Appl. Environ. Microbiol. 62:2676-2680), and the reverse primer S-*-Univ-0519-a-A-18 (519r: GWA TTA CCG CGG CKG CTG) (SEQ ID NO:16). For specific AOB DGGE, the forward primer of 358f (SEQ ID No:15) with a 40-bp GC-clamp on the 5' end was used with the reverse primer S-*-Ntros-0639-a-A-20 (Nitroso4e: CAC TCT AGC YTT GTA GTT TC) (SEQ ID NO:17). The PCR conditions were the same and were performed on a ROBOCYCLER GRADIENT 96 (Stratagene, La Jolla, Calif.) using the TAQ PCR core kit (Qiagen). PCR conditions included a hot start (80° C.) and a touchdown procedure. Initial denaturation at 94° C. for 3 min. was followed by a denaturation at 94° C. for 1 min., a touchdown annealing from 65° C. to 55° C. for 1 min. 29 sec. (the annealing time during the touchdown increased by 1.4 sec. per cycle) and primer extension at 72° C. for 56 sec. (the extension time was increased 1.4 sec. per cycle). The final temperature series of the above thermal cycle was repeated for 20 total cycles, followed by a final extension at 72° C. for 5 min. Amplicons were examined by agarose gel electrophoresis. DGGE was performed with a Bio-Rad D-GENE System (Bio-Rad Laboratories, Hercules, Calif.; hereinafter "Bio-Rad"). Gels were 8.5% acrylamide/Bis using Bio-Rad reagents (D GENE Electrophoresis Reagent Kit, Bio-Rad). Gel gradients were poured using Bio-Rad reagents (D GENE Electrophoresis Reagent Kit, Bio-Rad) with a denaturing gradient of 20% to 60% (where 100% denaturant is a mixture of 40% deionized formamide and 7 M urea) and the Bio-Rad gradient delivery system (Model 475, Bio-Rad). All gels were run at 200 volts for 6 hours. Gels were visualized in one of two ways. For visualization and recovery of discrete DNA bands, gels were first stained for 10 minutes in 250 ml of 1× TAE buffer in which 100 µl of ethidium bromide (1 mg/ml) was added, then washed for 10 min. in 1× TAE buffer. For documentation purposes some gels were stained in Vistra Green (diluted 1:10,000) (Molecular Dynamics, Sunnyvale, Calif.; hereinafter "Molecular Dynamics") for 20 min., followed by a 20 min. wash in 1× TAE buffer, and then scanned using a FLUORIMAGER SI (Molecular Dynamics).

Individual bands were excised from the DGGE gels using alcohol-sterilized scalpels. Extraction of DNA from the gel followed the methods of Ferris et al. (M. J. Ferris et al. 1996. Denaturing gradient gel electrophoresis profiles of 16S rRNA-defined population inhabiting a hot spring microbial mat community. Appl.Environ. Microbiol. 62: 340-346.). The excised band was placed in a sterile 2 ml screw cap tube with 500 µl sterile deionized water. The tubes were half-filled with glass beads (cat. no.11079-101, Biospec Products Inc., Bartlesville, Okla.; hereinafter "Biospec") and placed in a mechanical bead beater (MINI-BEADBEATER-8, Biospec) for 3 min. at the highest setting. The processed DNA remained in the tubes at 4° C. overnight. After overnight storage, the tubes were centrifuged at 3,200×g for 8 minutes at 4° C. to concentrate the gel fragments. The supernatant was transferred to a clean eppendorf tube.

To check the extraction efficiency, the supernatant was re-amplified with the DGGE primers and re-analyzed by DGGE. An extraction was considered acceptable if it yielded a single band in DGGE analysis which co-migrated with the original DGGE band in the mixed population sample. The nucleotide sequence of the excised band was sequenced by the previously described methods using fluorescently labeled primers.

Example 6

Oligonucleotide Probe Development

Oligonucleotide probes were designed that specifically hybridize with the 16S rRNA gene sequence isolated from closely related bacteria from reactors in this study. One probe (S-G-Nsspa-0149-a-A-18) (SEQ ID NO:5) targets two reactor-derived *Nitrosospira*-like bacteria, which are represented by the sequences of SEQ ID NO:1 and SEQ ID NO:2 to the exclusion of other beta subdivision Proteobacterial ammonia-oxidizers including the sequences represented by SEQ ID NO:3 and SEQ ID NO:4, and also to the exclusion of *Nitrosomonas aestuarii*-like bacteria represented by SEQ ID NO:18, SEQ ID NO:19 and SEQ ID NO:20.

A second probe (S-G-Nsspa-0149-a-A-19) (SEQ ID NO:8) targets one reactor-derived *Nitrosospira*-like bacterium, which is represented by the sequence of SEQ ID NO:3, to the exclusion of SEQ ID NO:1, SEQ ID NO:2, SEQ ID NO:4 and other beta subdivision Proteobacterial ammonia-oxidizers, and also to the exclusion of *Nitrosomonas aestuarii*-like bacteria represented by SEQ ID NO:18, SEQ ID NO:19 and SEQ ID NO:20.

Additional oligonucleotide probes were designed that specifically hybridize with the 16S rRNA gene sequence isolated from other bacteria from reactors in this study. One probe, S-G-Ntsms-0149-a-A-18, (SEQ ID NO:21) targets *Nitrosomonas aestuarii*-like bacteria, which are represented by the sequences of SEQ ID NO:18, SEQ ID NO:19 and SEQ ID NO:20 to the exclusion of other AOB sequences represented by SEQ ID NO:1, SEQ ID NO:2, SEQ ID NO:3, SEQ ID NO:4, as well as sequences from *halophila*-like bacteria.

Probe matches were initially screened using BLAST (S. F. Altschul et al. 1990. Basic local alignment tool. J. Mol. Biol. 215:403-410) and CHECK_PROBE (B. L. Maidak et al. 1994. The ribosomal database project. Nucleic Acids Res. 22:3485-3487.). Probes were synthesized by Operon Tech, Inc. (Alameda, Calif.). The nucleotide sequence and position of the probes are shown in Table 10.

TABLE 10

The nucleotide sequences and positions of oligonucleotide probes and PCR primer sets for ammonia-oxidizing bacteria.

| Probe/Primer | Base Sequence (5' to 3') | % formamide | Annealing Temp (° C.) | Target Group |
|---|---|---|---|---|
| S-G-Nsspa-0149-a-A-18 (SEQ ID NO: 5) | CCC CCC TCT TCT GGA TAC | 30 | — | SEQ ID NO: 1 & SEQ ID NO: 2 |
| S-G-Nsspa-0149-a-A-19 (SEQ ID NO: 8) | TCC CCC ACT CGA AGA TAC G | 20 | — | SEQ ID NO: 3 |
| S-G-Ntsms-0149-a-A-18 (SEQ ID NO: 21) | TCC CCC ACT TCT GGA CAC | 20 | — | SEQ ID NO: 18, SEQ ID NO: 19 & SEQ ID NO: 20 |
| Forward primer (SEQ ID NO: 6) | CGG AAC GTA TCC AGA AGA | — | 54 | SEQ ID NO: 1 & SEQ ID NO: 2 |
| Reverse primer (SEQ ID NO: 7) | ATC TCT AGA AAA TTC GCT | — | | |
| Forward primer (SEQ ID NO: 9) | ATC GGA ACG TAT CTT CG | — | 56 | SEQ ID NO: 3 |
| Reverse primer (SEQ ID NO: 10) | CCA CCT CTC RGC GGG C | — | | |
| Forward primer (SEQ ID NO: 11) | TCA GAA AGA AAG AAT CAT G | — | 56 | SEQ ID NO: 4 |
| Reverse primer (SEQ ID NO: 12) | GTC TCC AYT AGA TTC CAA G | — | | |
| Forward primer (SEQ ID NO: 22) | GTG ACT AAT AAT CAC AAC TTA | — | 56 | SEQ ID NO: 18, SEQ ID NO: 19 & SEQ ID NO: 20 |
| Reverse primer (SEQ ID NO: 23) | TTA TCT CTA AAA TAT TCG CT | — | | |

The stringency for the probes (SEQ ID NO:5, SEQ ID NO:8 and SEQ ID NO:21) was determined though a series of FISH experiments at differing formamide concentrations using the reactor biomass as a positive control for the bacterial sequences herein (SEQ ID NO:1, SEQ ID NO:2, SEQ ID NO:3, SEQ ID NO:4, SEQ ID NO:18, SEQ ID NO:19 or SEQ ID NO:20). The specificity of the probes was examined by testing against negative control cells of pure cultures of other beta subdivision ammonia-oxidizing bacteria (Nitrosomonas europaea, Nitrosospira multiformis, Nitrosomonas cryotolerans). In situ hybridization of the fixed, immobilized cells was carried out in a hybridization solution consisting of 0.9 M NaCl, 20 mM Tris/HCl (pH 7.4), 0.01% sodium dodecyl sulphate (SDS), 25 ng of oligonucleotide probe, and varying amounts of formamide. Slides were incubated in an equilibrated humidity chamber at 46° C. for 90 to 120 min. The hybridization solution was rinsed off with a prewarmed (48° C.) wash solution. The slides were then incubated in the wash solution for 15 min. at 48° C. To achieve the same stringency during the washing step, as in the hybridization step, the wash solution contained 20 mM Tris/HCl (pH 7.4), 0.01% SDS, 5 mM EDTA, and NaCl. The concentration of NaCl varied according to the percent formamide used in the solution. For 20% formamide the NaCl concentration was 215 mM, for 30% it was 120 mM, and for 40% the NaCl concentration was 46 mM. Cells were detected using an AXIOSKOP 2 epifluorescence microscope (Carl Zeiss, Jena, Germany) fitted with filter sets for FITC/FLUO3 and HQ CY3. The optimum stringency was determined to be 30% formamide for the S-G-Nsspa-0149-a-A-18 probe. For the S-G-Nsspa-0149-a-A-19 probe the optimum stringency was determined to be 20% formamide. The optimum stringency was determined to be 20% formamide for the probe represented by SEQ ID NO:21, and 20% formamide for the probe represented by SEQ ID NO:24.

Example 7

PCR Primer Development

Two sets of PCR primers were developed which specifically detect Nitrosospira-like bacteria of the sequences of the present invention. A third set of PCR primers was developed which specifically detects Nitrosomonas-like bacteria of the sequences of the present invention. One set (SEQ ID NO:6 and SEQ ID NO:7) specifically detects Nitrosospira-like bacteria with the sequence SEQ ID NO:1 and sequence SEQ ID NO:2 to the exclusion of other ammonia-oxidizing bacteria (Table 11). The second set (SEQ ID NO:9 and SEQ ID NO:10) specifically detects the Nitrosospira-like bacteria with the sequence SEQ ID NO:3 to the exclusion of other ammonia-oxidizing bacteria (Table 11). The third set (SEQ ID NO:11 and SEQ ID NO:12) specifically detects the Nitrosomonas-like bacteria with the sequence SEQ ID NO:4 to the exclusion of other ammonia-oxidizing bacteria (Table 11).

A fourth set (SEQ ID NO:22 and SEQ ID NO:23) specifically detect the Nitrosomonas aestuarii-like bacteria with the sequences SEQ ID NO:18, SEQ ID NO:19 and SEQ ID NO:20 to the exclusion of other ammonia-oxidizing bacteria. PCR conditions were as previously described except the annealing temperature was modified.

The specificity of each primer set was optimized by conducting a PCR experiment with each primer set using the temperature gradient mode of the Stratagene ROBOCYCLER. In this mode one can run a single experiment of all the reactions at up to 12 different annealing temperatures. Typically, the experiments were conducted at 4 to 6 different temperatures with 2° C. increasing interval. Each PCR primer set was tested against clone product with a nucleotide sequence of SEQ ID NO:1, SEQ ID NO:2, SEQ ID NO:3, SEQ ID NO:4, SEQ ID NO:18, SEQ ID NO:19 and SEQ ID NO:20. rDNA extracted from pure cultures of *Nitrosomonas europaea*, *Nitrosolobus multiformis* and *Nitrosomonas cryotolerans*, were also tested. Table 10 presents the PCR primer sets, and the optimal annealing temperature results are shown in Table 11.

TABLE 11A

Results of the PCR primer development specificity testing and annealing temperature experiments.

| Clone Number or Bacteria Species | Type A AOB PCR SEQ ID NO: 6 and SEQ ID NO: 7 | | | | Type B AOB PCR SEQ ID NO: 9 and SEQ ID NO: 10 | | | | Type C AOB PCR SEQ ID NO: 11 and SEQ ID NO: 12 | | | | |
|---|---|---|---|---|---|---|---|---|---|---|---|---|---|
| Annealing Temp. (° C.) | 48 | 50 | 52 | 54 | 54 | 56 | 58 | 60 | 48 | 50 | 52 | 54 | 56 |
| R7c140 (TypeA) | + | + | + | + | − | − | − | − | − | − | − | − | − |
| R7c187 (TypeA) | + | + | + | + | − | − | − | − | − | − | − | − | − |
| R3c5 (TypeB) | − | − | − | − | + | + | + | + | − | − | − | − | − |
| R5c20 (TypeB) | − | − | − | − | + | + | + | + | − | − | − | − | − |
| R3c12 (TypeC) | − | − | − | − | − | − | − | − | + | + | + | + | + |
| R5c47 (TypeC) | − | − | − | − | − | − | − | − | + | + | + | + | + |
| *N. europaea* | − | − | − | − | − | − | − | − | − | − | − | − | − |
| *N. multiformis* | − | − | − | − | − | − | − | − | +/− | +/− | +/− | − | − |
| *N. cryotolerans* | − | − | − | − | − | − | − | − | − | +/− | + | +/− | − |
| P4c42 | − | − | − | − | − | − | − | − | − | − | − | − | − |
| P4c31 | − | − | − | − | − | − | − | − | − | − | − | − | − |
| BF16c57 | − | − | − | − | − | − | − | − | − | − | − | − | − |
| Negative control | − | − | − | − | − | − | − | − | − | − | − | − | − |

Weak (+/−),
Strong (+) or
No Signal (−)

TABLE 11B

Results of the PCR primer development specificity testing and annealing temperature experiments.

| Clone Number or Bacteria Species | SEQ ID NO: 22 and SEQ ID NO: 23 | | | |
|---|---|---|---|---|
| Annealing Temp. (° C.) | 48 | 50 | 52 | 54 |
| R7c140 (TypeA) | − | − | − | − |
| R7c187 (TypeA) | − | − | − | − |
| R3c5 (TypeB) | − | − | − | − |
| R5c20 (TypeB) | − | − | − | − |
| R3c12 (TypeC) | − | − | − | − |
| R5c47 (TypeC) | − | − | − | − |
| *N. europaea* | − | − | − | − |
| *N. multiformis* | − | − | − | − |
| *N. cryotolerans* | − | − | − | − |
| P4c42 | − | − | − | − |
| P4c31 | − | − | − | − |
| BF16c57 | − | − | − | − |
| Negative control | − | − | − | − |

Weak (+/−),
Strong (+) or
No Signal (−)

Example 8

Similarity Analysis

Thirteen clone libraries were constructed from a number of freshwater and saltwater nitrifying biomasses in order to determine the identity of the ammonia oxidizer(s) responsible for oxidation of ammonia to nitrite. Details about the biomasses are presented in Table 12.

TABLE 12

Details regarding the reactors and aquaria from which biomass was extracted and clone libraries was constructed.

| Clone library | Details of Nitrifying Biomass |
|---|---|
| Biofarm 16 | This biomass was retrieved from the sump of BF16. The biofarm was routinely dosed 300 mg/L/hr of ammonia (NH$_3$—N) for 6 hours per day. |

TABLE 12-continued

Details regarding the reactors and aquaria from which biomass was extracted and clone libraries was constructed.

| Clone library | Details of Nitrifying Biomass |
|---|---|
| BC5 | This biomass was kept in an aquarium (seeded from a freshwater biofarm) and dosed 5 mg/L or less of ammonia every two or three days. The aquarium was not aerated. |
| BC5(2) | Same as BC5 (above). |
| R3 | This was seeded from an enriched ammonia oxidizing culture (approx 1000 mg/L $NH_3$—N) that had been stored for 11 months. Grown at 5 mg/L $NH_3$—N and aerated. |
| R7 | This was seeded from R1 which had been seeded from BC5. Both R1 and R7 were kept below 5 mg/L ammonia ($NH_3$—N) and aerated. |
| R7BA6 | This biomass was recovered from a Bacterial Additive test that was inoculated with R7 biomass. |
| R5 | This biomass was derived from the biofarm feed microfilter. It was exposed to extremely high concentrations of ammonia (>500 mg/L $NH_3$—N). The reactor was operated at 30 mg/L ammonia ($NH_3$—N) and aerated. |
| R17 | This biomass was derived from R7 but fed at 30 mg/L for a period of three weeks before being returned to 5 mg/L ammonia, aerated. |
| R13 | This biomass was derived from the BC5 biomass but did not appear to have any Nitroso- bacteria by using general AOB primers. It was grown at 5 mg/L ($NH_3$—N) and aerated. |
| R29 | This biomass was retrived from the sump of biofarm 5 which was a saltwater biomass whose salinity was maintained at between 30 and 35 ppt. This reactor was fed at 30 mg/L ammonia-nitrogen. |
| P4 | This reactor was seeded with 20 liter of material from the sump of biofarm 15 which was a saltwater biomass whose salinity was maintained at between 30 and 35 ppt. This reactor was fed at 5 mg/L ammonia-nitrogen. |
| SB7 | This reactor was seeded with material from the sumps of biofarm 5 and 15 which were saltwater biomasses whose salinity was maintained at between 30 and 35 ppt. This reactor was fed at 5 mg/L ammonia-nitrogen. |
| B7 | This reactor was seeded with material from the sumps of biofarm 5 and 15 which were saltwater biomasses whose salinity was maintained at between 30 and 35 ppt. This reactor was fed at 5 mg/L ammonia-nitrogen. |

The clone library data show that there are three groups of ammonia oxidizing bacteria that exist in the low ammonia feed reactors (e.g., R3, R7). Not all three AOB types were found to exist in every reactor though. The three bacteria are represented by three AOB clone groups—AOB Type A (SEQ ID NO:1) (and a subtype A1 (SEQ ID NO:2)), and AOB Type B (SEQ ID NO:3). A fourth clonal type was found in high ammonia feed reactors—AOB Type C (SEQ ID NO:4).

A similarity ranking was conducted for the four clonal sequences using RDP (Maidak, B. L., J. R. Cole, C. T. Parker, Jr, G. M. Garrity, N. Larsen, B. Li, T. G. Lilburn, M. J. McCaughey, G. J. Olsen, R. Overbeek, S. Pramanik, T. M. Schmidt, J. M. Tiedje and C. R. Woese. A new version of the RDP (Ribosomal Database Project). Nucleic Acids Res. 27:171-173 (1999)) (Table 8). The similarity analysis showed that AOB Type A (SEQ ID NO:1) and Type A1 (SEQ ID NO:2) are 99.6% similar. This agrees with the 16S rDNA data which showed there to be 5 mismatches in the 16Sr DNA between the type sequence for Type A (SEQ ID NO:1) and the type sequence for Type A1 (SEQ ID NO:2). The similarity analysis showed that the Type A and A1 sequences are significantly different from known AOBs of either the *Nitrosospira* or *Nitrosomonas* clades (Table 13). This result is further supported by the Bootstrap analysis which shows that the AOB Type A (SEQ ID NO:1) and Type A1 (SEQ ID NO:2) cluster together in a group that is distinct from either the *Nitrosospira* or *Nitrosomonas* clades (FIG. 1). Thus the bacteria represented by AOB Type A (SEQ ID NO:1) and Type A1 (SEQ ID NO:2) are at least new species.

TABLE 13

Similarity ranking for the ammonia-oxidizing clones isolated from reactors and aquaria

| rDNA source | % Similarity to rDNA of: | | | | | | | | | |
|---|---|---|---|---|---|---|---|---|---|---|
| | Type A Nitrospira-like | Type A1 Nitrospira-like | Type B Nitrospira-like | Type C Nitrosomonas-like | *Nitrosomonas marina* | *Nitrosovibrio tenuis* | *Nitrosolobus multiformis* | *Nitrosospira briensis* | *Nitrosomonas europaea* | *Nitrosococcus mobilis* |
| Type A Nitrospira-like | — | | | | | | | | | |

TABLE 13-continued

Similarity ranking for the ammonia-oxidizing clones isolated from reactors and aquaria

| rDNA source | % Similarity to rDNA of: | | | | | | | | |
|---|---|---|---|---|---|---|---|---|---|
| Type A1 Nitrosospira-like | 0.996 | — | | | | | | | |
| Type B Nitrosospira-like | 0.944 | 0.942 | — | | | | | | |
| Type C Nitrosomonas-like | 0.934 | 0.932 | 0.925 | — | | | | | |
| Nitrosomonas marina | 0.954 | 0.955 | 0.928 | 0.932 | — | | | | |
| Nitrosovibrio tenuis | 0.948 | 0.946 | 0.988 | 0.926 | 0.932 | — | | | |
| Nitrosolobus multiformis | 0.948 | 0.946 | 0.984 | 0.927 | 0.937 | 0.989 | — | | |
| Nitrosospira briensis | 0.941 | 0.940 | 0.971 | 0.919 | 0.936 | 0.979 | 0.980 | — | |
| Nitrosomonas europaea | 0.936 | 0.935 | 0.925 | 0.984 | 0.932 | 0.931 | 0.933 | 0.925 | — |
| Nitrosococcus mobilis | 0.942 | 0.939 | 0.921 | 0.962 | 0.930 | 0.928 | 0.931 | 0.930 | 0.962 |

| | P4c31 Nsm. aest.-like | P4c42 Nsm. aest.-like | BF16c57 Nsm. sp. AF386746 | R7c140 Nsm. sp. AF386753 | Nsm. halophila AF272413 | Nsm. aestuarii AF272420 | Nsm. marina M96400 | Marine bact. NO3W AF33820 | Nsm. sp. NM51 AF272424 |
|---|---|---|---|---|---|---|---|---|---|
| P4c31 Nsm. aestuarii-like | — | | | | | | | | |
| P4c42 Nsm. aestuarii-like | 0.966 | — | | | | | | | |
| BF16c57 Nsm. sp. (AF386746) | 0.972 | 0.976 | — | | | | | | |
| R7c140 Nsm. sp. (AF386753) | 0.981 | 0.981 | 0.983 | — | | | | | |
| Nsm. halophila (AF272413) | 0.914 | 0.914 | 0.916 | 0.947 | — | | | | |
| Nsm. aestuarii (AF272420) | 0.983 | 0.977 | 1.000 | 0.983 | 0.916 | — | | | |
| Nsm. marina (M96400) | 0.971 | 0.971 | 0.973 | 0.971 | 0.937 | 0.973 | — | | |
| Marine bact. NO3W (AF33820) | 0.994 | 0.994 | 0.996 | 0.980 | 0.944 | 0.996 | 0.974 | — | |
| Nsm. sp. NM51 (AF272424) | 0.951 | 0.959 | 0.982 | 0.979 | 0.915 | 0.982 | 0.989 | 0.981 | — |

The similarity analysis for the AOB Type B (SEQ ID NO:3) shows that this bacterium falls into *Nitrosospira* clade of AOB (Table 13). Bootstrap analysis confirms this result (FIG. 1).

However, the organism is distinct enough from the closest *Nitrosospira* AOB (*Nitrosovibrio tenuis*) that it may be considered as a new species.

The similarity analysis for the AOB Type C (SEQ ID NO:4) shows that this bacterium falls into *Nitrosomonas* clade of AOB (Table 13). Bootstrap analysis confirms this result (FIG. 1). However, the organism is distinct enough from the closest *Nitrosomonas* AOB (*Nitrosomonas europaea*) that it may be considered as a new species.

Figure 6:
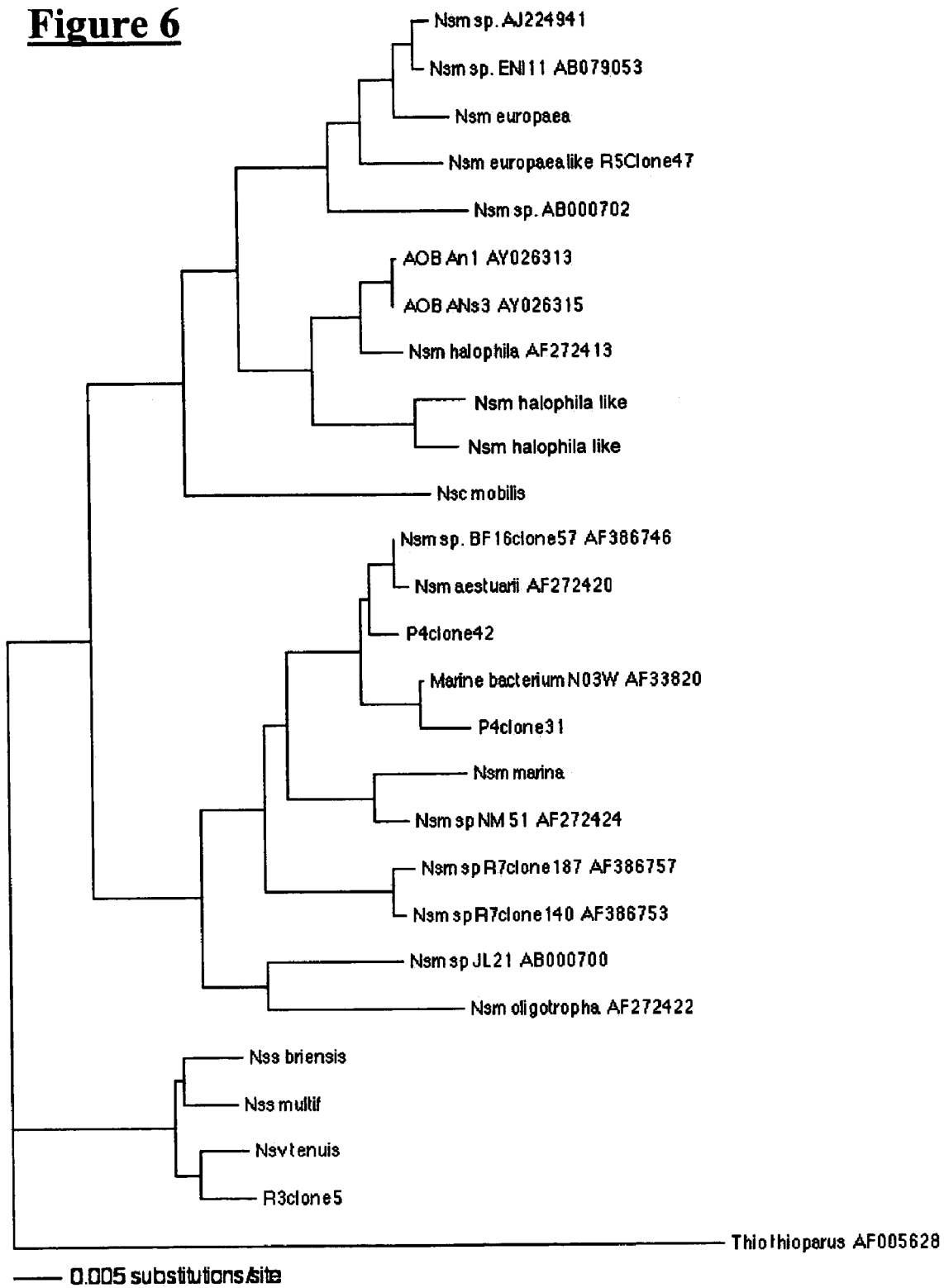
FIG. 6 illustrates the phylogenetic relationships of two bacterial strains (i.e., those represented by SEQ ID NO:18 and SEQ ID NO:19), and one substrain (i.e., that represented by SEQ ID NO:20) inferred from comparative analysis of 16S rDNA sequences in accordance with an embodiment of the present invention. The tree further depicts the relationship among the two bacterial strains represented by SEQ ID NO:18 and SEQ ID NO:19 and the bacterial strains represented by SEQ ID NO:1, SEQ ID NO:2, SEQ ID NO:3 and SEQ ID NO:4. The tree is based on neighbor-joining distance analysis of sequences containing a minimum of 1430 nucleotides.

The similarity analysis for the saltwater tolerant AOB we isolated which are *Nitrosomonas aestuarii*-like reveals clone P4c31 (SEQ ID NO:19) to be 98.3% similar to *Nitrosomonas aestuarii* and clone P4C42 (SEQ ID NO:18) is 97.7% similar to *Nitrosomonas aestuarii*. Phylogenetic analysis demonstrates the uniqueness of the sequences represented by clones P4C42 (SEQ ID NO:18) and P4c31 (SEQ ID NO:19) (FIG. 6).

The similarity rankings given in Table 13 are a guide to determining the uniqueness of one bacterial strain to another. There are no hard and fast rules regarding what percentage constitutes a new species. However, *Nitrosolobus multiformis* and *Nitrosovibrio tenuis* which have a similarity ranking of 0.989 are recognized by all microbiological authorities as distinct species, as are *Nitrosolobus multiformis* and *Nitrosospira briensis* (similarity ranking of 0.980). Since the similarity values of the bacterial strains reported herein are not higher than those for the above mentioned species pairs this is further evidence that the strains herein are novel and unique.

Therefore, the totality of the clone data, the PCR results, the phylogenetic analysis, the DGGE data and similarity ranking demonstrate that the bacterial strains reported herein are unique and distinct from known ammonia-oxidizing bacteria. Further, we expect that additional work in micro (or specialized) environments such as presented herein will result in the discovery of additional AOB related to the strains reported herein.

Example 9

Analysis of Bacteria and Experimental Results

Figure 2:
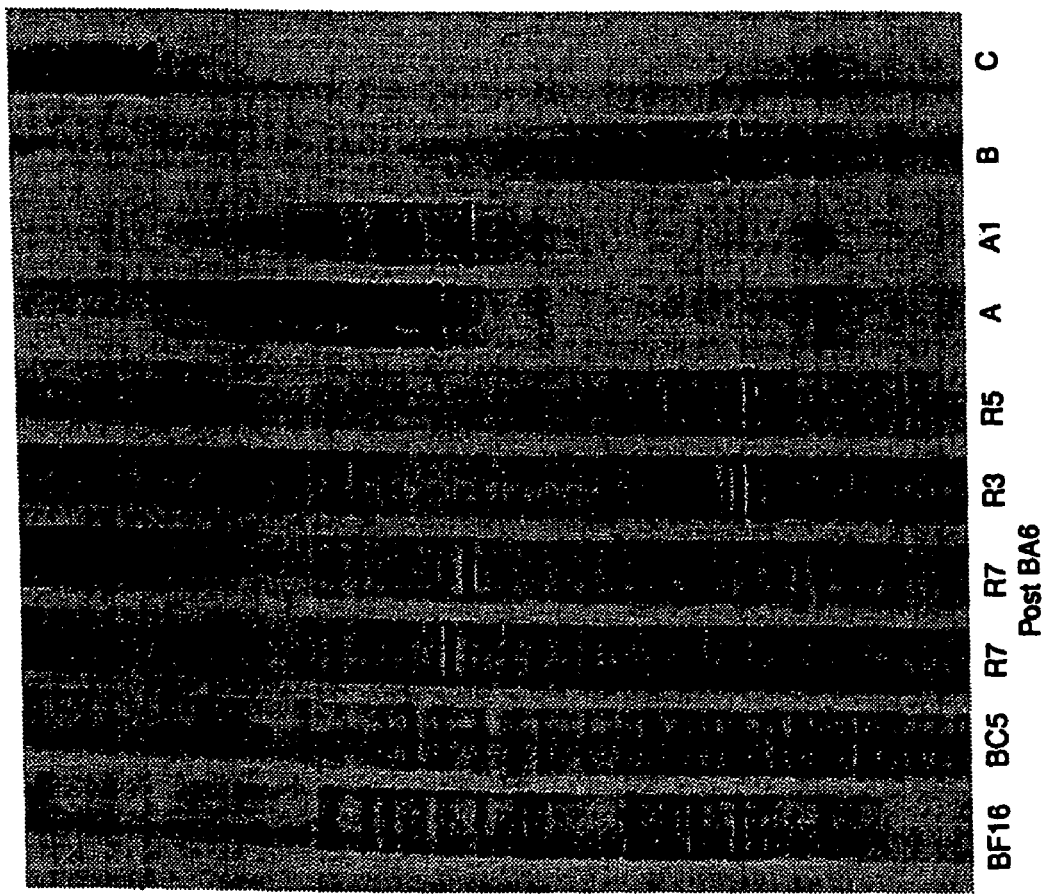
FIG. 2 illustrates a denaturing gradient gel electrophoresis (DGGE) of biomasses from selected cultures and ammonia-oxidizing bacteria represented by SEQ ID NO:1, SEQ ID NO:2, SEQ ID NO:3 and SEQ ID NO:4, in accordance with an embodiment of the present invention.

Clonal members of Type A AOB (SEQ ID NO:1 and SEQ ID NO:2) were found in both the BF16 biomass (9% of clone library) and the BC5 biomass (1-2% of clone library) (FIG. 2). The BC5 biomass was used to seed the low concentration ammonia reactor (R1), which was used to seed R7. The R7 clone library generated from the R7 biomass containing only Type A AOB clones (SEQ ID NO:1 and SEQ ID NO:2) (7% of the clone library) (FIG. 2). Hence Type A AOB bacteria have been successfully subcultured from the freshwater Biofarm to the BC5 tank and then in the R7 reactor via the R1 reactor. This demonstrates the ability to successively culture the bacteria and to maintain a viable culture of AOB with the sequences herein. Further, it demonstrates the ability to selectively enrich for the Type A AOB as the percent of this bacterium increased from 1-2% in the BC5 clone library to 7% in the R7 library.

Outwardly, the operation of the three systems (BioFarm 16, BC5 tank, and R7 reactor) would appear to be quite different (see Table 12). However, there is a common set of physicochemical conditions that may explain the presence of Type A AOBs in these systems. Although the Biofarm receives high concentrations of ammonia initially, it is allowed a period of time for the ammonia concentrations to fall to low levels (below 5 mg/L $NH_3$—N), thus allowing the Type A bacteria to be retained in the system, exploiting a particular physiological niche of being able to grow at very low ammonia concentrations (<5 mg/L $NH_3$—N). Similarly, the BC5 tank and the R7 reactor were both fed and maintained at ammonia levels at or below 5 mg/L $NH_3$—N. The Type A AOB bacteria may be able to exist at ammonia concentrations above 5 mg/L $NH_3$—N but it is apparent that at higher concentrations of ammonia they are outcompeted by other types of AOBs (i.e., Type B (SEQ ID NO:3) and/or Type C (SEQ ID NO:4)) as evidenced by these types of AOB being present, and Type A AOB being absent, in the reactors maintained at high ammonia concentrations (Table 14) (FIG. 2).

The R7 biomass did particularly well in the bacterial additives test VI (BA6) and VII (BA7) (discussed below) as did a biomass grown in the same fashion (R19) and with the same seed (R1) in bacterial additives test VIII (BA8) (R19). Type A AOBs have been found in a number of reactors and a number of Post BA test biomasses both by specific Type A AOB PCR and FISH tests (Table 14) (FIG. 2).

Therefore, these two newly discovered bacteria Type A AOB (SEQ ID NO:1) and Type A1 (SEQ ID NO:2) predominate in low ammonia concentration environments, such as aquaria; and, when added to such an environment in a more purified state than they naturally occur, can accelerate the establishment of ammonia oxidation in such an environment (discussed below).

Clonal members of Type B were found in the freshwater BioFarm biomasses (e.g., BF 16-34% of clone library) used to seed the BC tanks (BC5). Type B AOB bacteria were absent in the BC5 and R7 clone libraries, indicating that these AOBs may be more suited to the high ammonia conditions and feeding regime of a Biofarm (FIG. 2). Type B AOBs were also found in the R3 clone library (19% of clone library) (FIG. 2). The history of the R3 reactor is that its biomass was initially enriched at high ammonia concentrations (3000 mg/L $NH_3$—N), stored for 11 months and then matured in the reactor at low ammonia concentrations (5 mg/L $NH_3$—N) for an extended period of time. During the initial culturing period it was likely that the ammonia concentrations would decrease over time—thus encouraging the growth of Type C and/or Type B AOBs over Type A AOBs. During the eleven months of storage the ammonia would be likely to be exhausted possibly encouraging the maintenance of Type B AOB bacteria in the system and the survival of residual Type A AOBs that had survived during the culturing phase. Finally during the maturation period in the reactor, the Type B AOB bacteria would be able to be maintained, Type A AOBs would be enriched and any residual Type C that had been originally selected for in the original culturing phase would be outcompeted and disappear.

In comparison, the Biofarm's biomass receives a relatively high concentration of ammonia for a set period of time and then allowed to gradually deplete this over time, creating both a gradient of high to low ammonia concentrations (encouraging the growth of Type B AOBs), often reaching zero thus allowing a window for the growth of Type A AOBs—low ammonia concentrations. This is a more rapid cycle (daily) than the culturing phase of the R3 biomass, but none the less consistent with a change of conditions from high to low ammonia concentrations within the biomass. Thus the gradient of ammonia concentrations in the Biofarm's biomass encourages the enrichment of a range of AOB types as confirmed by the clone library data and the results of the DGGE tests.

Type B AOBs have been found in a number of reactors and a number of Post BA test biomasses both by specific Type B AOB PCR, DGGE and FISH. However, it has not been found in as many post bacterial additive tests or clone libraries as Type A AOB (Table 14). It seems to be that if Type A AOB was inoculated into a test it was often recovered whereas Type B AOBs were only recovered in systems where Type A AOBs were not originally in the innoculum. Therefore, Type A AOBs are preferentially grown in the systems when they are present but Type B AOBs will suffice when Type A AOBs are absent.

While Type A AOBs are the most important member of a successfull AOB nitrifying community for low ammonia environments such as aquarium, they are not the only AOB present. Other AOB, such as Type B (SEQ ID NO:3), may be necessary for the system to efficiently cope with fluctuating concentrations of ammonia even over short (days) periods of time.

Type C AOBs are not desirable as an AOB in a bacterial additive for the low ammonia concentrations typically found in an aquarium. Type C AOB bacteria were not found in the BF16, BC5 or R7 clone libraries which are low ammonia concentration environments, indicating that they were likely grown under conditions other than that found in these three environments (FIG. 2). Type C bacteria were found in the R5, R3 and R17 clone libraries (FIG. 2). The R5 biomass was grown consistently at high concentrations (30 mg/L $NH_3$—N) and its seed was from a very high ammonia concentration (>500 mg/L NH$_3$—N), R3's biomass had been originally grown at a high ammonia concentration before being moved to a lower ammonia concentration (5 mg/L NH$_3$—N) and the R17 biomass was moved from a low (5 mg/L NH$_3$—N) to a high ammonia concentration (30 mg/L NH$_3$—N) and then back again.

The R5 biomass had been enriched at high ammonia concentrations for a long period of time even before being transferred to the R5 reactor, in effect excluding the growth of any Type A AOB bacteria as the concentration of ammonia never dropped to low levels in the feed microfilter. When the biomass was transferred to R5 and the concentration of ammonia was reduced to lower levels Type B AOB were enriched for and became the dominant AOB in this culture. The Type C bacteria would represent the bacteria enriched for initially in the microfilter and then remained in the R5 biomass when the feed was kept at relatively high ammonia concentrations (30 mg/L NH$_3$—N).

The R3 biomass had been initially allowed to grow at high ammonia concentrations but over time the ammonia would become exhausted. This regime initially encourages the growth of Type C AOBs (at higher ammonia concentrations) and Type B AOBs (as the ammonia was utilized). Further, these pressures would not allow for the enrichment of Type A AOB which are dependent on consistently low levels of ammonia. During the operation of the R3 reactor at lower ammonia concentrations, Type C AOB bacteria would be enriched against and Type B would still survive but since Type A AOB bacteria were originally minimized in the initial enrichment there would be very few left to take advantage of the new conditions within the reactor. Therefore, Type B AOB would be expected to be the dominant AOB in this environment.

The R17 biomass shows typically what not to do for culturing Type A and/or B AOBs. The R17 biomass was derived from the R7 biomass but cultured for 3 weeks at elevated ammonia (30 mg/L NH$_3$—N) concentrations to see if a shift in the microbial community would occur. A shift did occur and Type C AOBs became dominant, as demonstrated by the results of FISH, PCR and DGGE experiments. Furthermore, the shift was irreversible. After moving the biomass back to a low ammonia concentration (5 mg/L NH$_3$—N) environment, the Type C AOB still remained the dominant AOB while Type A and Type B AOBs could not be detected by either FISH or DGGE. This suggests that during the three week period Type A and B AOBs were excluded from the R17 biomass. The R17 biomass did poorly in the subsequent BA VIII test suggesting that Type C AOBs are not the correct type of AOB required for an effective bacterial additive to be used in the relatively low ammonia environment of an aquarium. This conclusion is further supported by the results of the bacterial additive tests which showed that existing commercial bacterial mixtures which contain *Nitrosomonas* lade AOBs are not effective for accelerating the establishment of nitrification in aquaria (discussed below).

The Type C bacteria are very closely related phylogenetically to those bacteria that have been found in wastewater treatment plants which also receive ammonia concentrations of around 30 mg/L NH$_3$—N (similar to R5).

The PCR primer sets described herein were used to detect the presence or absence of the AOB strains reported here in a variety of environments. The environments include pre bacterial additive test mixtures, post bacterial additive test aquaria filters, and commercial mixtures of nitrifying bacteria manufactured and sold by other companies. In addition, DNA extracted from the pure culture of other AOB was tested.

The results of these experiments are summarized in Table 14. The data show that the PCR primer groups are specific for the bacterial strain reported herein and allow one to detect each strain exclusive of the other strains. Further, pure cultures of known AOB are not amplified with any of the PCR primer sets reported herein. This demonstrates that the bacteria reported herein can be distinguished from known AOB.

The data also show that one would expect the commercial additives currently on the market to fail in accelerating the establishment of nitrification in newly set-up aquaria because these additives do not contain the correct species of bacteria (further detailed in the following section).

Example 10

Denaturing Gradient Gel Electrophoresis Survey of Clones and Reactors

Figure 3:
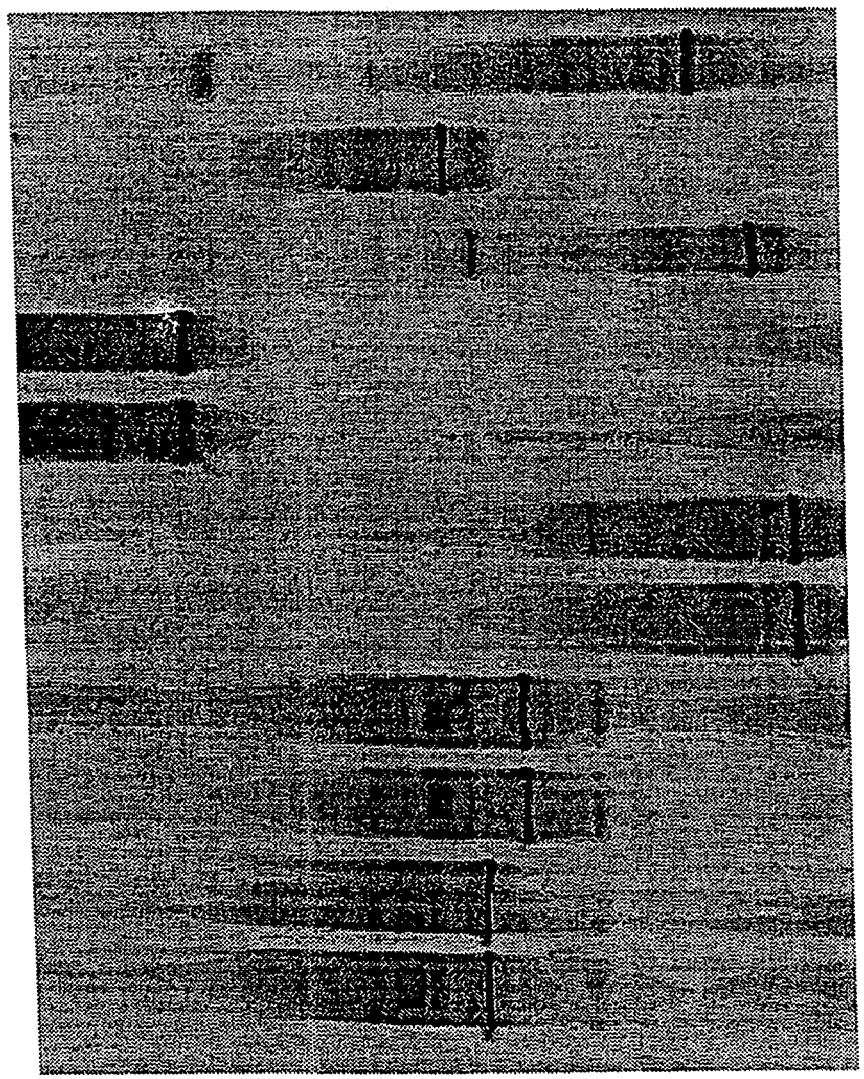
FIG. 3 illustrates a DGGE demonstrating the uniqueness of the bacterial strains represented by SEQ ID NO:1, SEQ ID NO:2, SEQ ID NO:3 and SEQ ID NO:4, in accordance with an embodiment of the present invention. There are two replicates of each aforementioned bacterial type along with extracts from three pure cultures of ammonia-oxidizing bacteria.

The novelty of various bacterial strains reported herein is further demonstrated by the results of the denaturing gradient gel electrophoresis (DGGE) testing. FIG. 3 shows the DGGE results for two clone representatives for each of the Type A AOB (SEQ ID NO:1), Type A1 AOB (SEQ ID NO:2), Type B AOB (SEQ ID NO:3) and Type C AOB (SEQ ID NO:4) in a general eubacterial DGGE. The bacterial sequence of each AOB Type described herein denatures at a different position in the gel. This is indicative of uniqueness and provides another means by which to distinguish each AOB Type from one another and also from known AOB. None of the bacterial sequences noted above co-migrated with *Nitrosomonas europaea*, *Nitrosospira multiformis* or *Nitrosomonas cryotolerans* (FIG. 3). Furthermore, DGGE analyses of biomass extracted from various reactors confirmed the results of the PCR and FISH testing.

Figure 7:
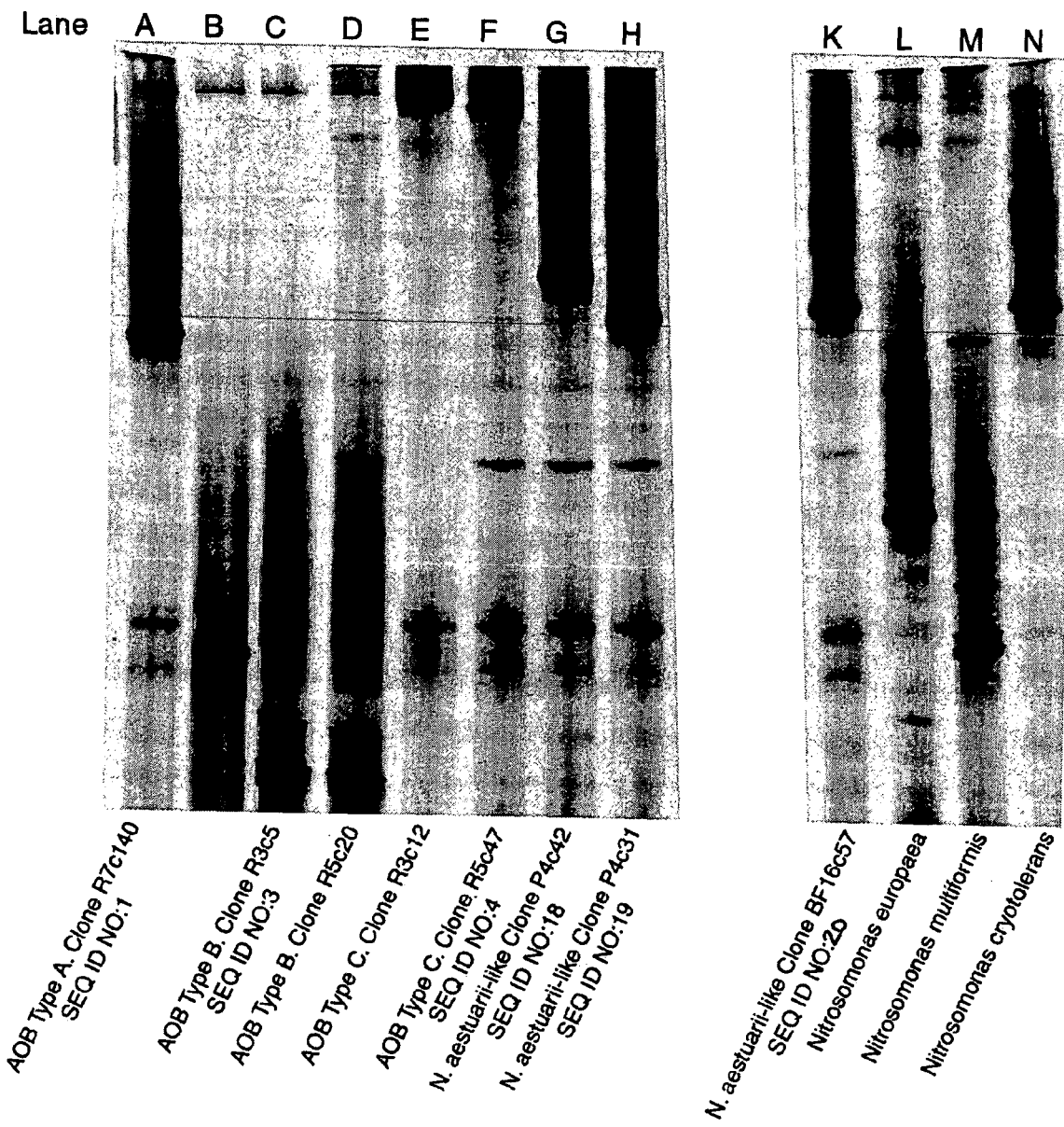
FIG. 7 illustrates a denaturing gradient gel electrophoresis (DGGE) of the biomasses from selected freshwater cultures of ammonia-oxidizing bacteria represented by SEQ ID NO:1, SEQ ID NO:3 and SEQ ID NO:4 along with seawater cultures of ammonia-oxidizing bacteria represented by SEQ ID NO:18, SEQ ID NO:19 and SEQ ID NO:20 and pure cultures of the ammonia-oxidizing bacteria *Nitrosomonas europaea, Nitrosomonas multiformis*, and *Nitrosomonas cryotolerans*.

FIG. 7 presents DGGE results that further distinguish the various AOB strains of the present invention. Bands representing *Nitrosomonas aestuarii*-like clones P4c42 and P4c31 (SEQ ID NO:18 and SEQ ID NO:19) do not co-migrate with bands representing the strains of AOB of Type A AOB (SEQ ID NO:1), Type B AOB (SEQ ID NO:3), Type C AOB (SEQ ID NO:4) and *Nitrosomonas aestuarii*-like clone BF16c57 (SEQ ID NO:20). None of these strains co-migrated with *Nitrosomonas europaea*, *Nitrosospira multiformis* or *Nitrosomonas cryotolerans* (FIG. 7).

Example 11

Bacterial Additive Tests

A series of experiments were conducted to determine the efficacy of various bacterial mixtures containing the bacterial strains of the present invention as compared to: (1) control aquaria that did not receive a mixture, (2) aquaria that were inoculated with bacterial mixtures for use in tropical fish aquaria, and (3) preserved or stored bacterial mixtures of the bacterial strains of the present invention.

Effectiveness of a mixture is demonstrated by showing that the ammonia-oxidizing bacterial strains of the present invention oxidize ammonia in aquaria and, further, that when combined with other bacterial. strains (e.g., nitrite-oxidizing bacteria), the bacteria accelerate the establishment of nitrification in aquaria. Establishment of nitrification can be measured in at least three different ways. The first is by counting the number days it takes after establishing a new aquarium for the ammonia and nitrite concentrations in the aquarium water to reach a near 0 mg/L concentration. In a newly set-up freshwater aquarium, it typically takes about 14 days for the ammonia concentration to reach 0 mg/L and about 30 to 35 days for nitrite to reach 0 mg/L.

A second way to measure the beneficial action of adding nitrifying bacterial strains to aquaria is to compare the maximum concentration of ammonia or nitrite reached before the concentration drops to 0 mg/L. If the maximum concentration of ammonia or nitrite reached in aquaria in which nitrifying bacteria were added is significantly less than the maximum concentration reached in control aquaria, then a degree of effectiveness is demonstrated.

A third way to evaluate the effectiveness of nitrifying bacterial strains and mixtures that incorporate them is to combine the first two methods to form a toxicity exposure curve. This type of curve accounts for both the duration (time in days) and the degree/intensity of the exposure. In accordance with embodiments of the present invention, this curve is generated by plotting the concentration of the toxin over time. The area of the curve may then be determined for each treatment and toxin by standard computational methods (e.g., by mathematically integrating the curve). The treatments of each test are then compared to one other and to the control of the same test. The control curve area can be given an arbitrary value of 1 and the other areas may thereafter be calculated as a ratio to the control area. As such, if the value of a treatment is greater than 1 it is deemed more effective than the control, while a value of less than 1 suggests that it is less effective than the control and may have inhibited the establishment of nitrification.

Example 12

Bacterial Additive Test VI

The goal of this test was to evaluate the ability of four bacterial mixtures, including bacterial strains of the present invention, to accelerate the establishment of nitrification in freshwater aquaria. The test was also conducted to compare an ability to establish nitrification among the bacterial strains of the present invention and control aquaria which did not receive a bacterial inoculation of any kind.

Twenty-seven ten-gallon aquaria and twenty-seven Penguin 170B (Marineland Aquarium Products) hang-on-the-back style power filters were sterilized, thoroughly rinsed, and allowed to air dry. Each aquarium was then filled with 10 lbs of rinsed aquarium gravel (RMC Lonestar #3) and the filter installed. The aquaria then received 35 l of city tap water which had been filtered through activated carbon. After turning the filters on, the water level on each aquarium was marked so all could be topped-off with deionized water (DI) to account for any water loss due to evaporation and sampling. The filters ran overnight prior to the addition of the bacterial additives and fish.

On day 0 of the test, the aquaria were topped off with DI water and a baseline water sample taken for analysis. Carbon cartridges (Marineland Aquarium Products, Part No. PA 0133) were rinsed with tap water and placed in each filter. New BIOWHEELS (Marineland Aquarium Products, Part No. PR 1935B) were placed in each filter. After thirty minutes each tank was inoculated with its designated bacterial additive, or, if the tank was a control aquarium, it was not dosed with a bacterial mixture.

Thirty minutes after the experimental bacterial additives were added, a second set of water samples were taken for analysis. Five rosy barbs (*Puntius conchonius*) and one giant danio (*Danio aequipinnatus*) were then added to each tank. The fish were fed approximately 0.4 grams of tropical fish flake split into two feedings per day (at approximately 9:00 a.m. and 4:30 p.m.).

Water samples were collected and analyzed tested daily for pH, ammonia, nitrite and conductivity. On Monday, Wednesday and Friday the water was tested for nitrate and turbidity. Anions and cations were measured periodically. Measurements for pH were made with a Denver Instruments Model 225 pH/Ion meter equipped with a Denver Instruments pH combination electrode. A Tecator FIAstar 5010 Analyzer was used to measure ammonia, nitrite and nitrate (i.e., as nitrogen) using methods described in Tecator Application Notes. Cations (sodium, ammonium-nitrogen, potassium, magnesium and calcium) were analyzed using a Dionex DX500 System with a CS15 4-mm Analytical Column. Specific conductance was measured directly in each tank at approximately 12:30 p.m. daily using a YSI Model 30 hand-held salinity, conductivity and temperature system. Turbidity data was determined with a DRT-100 turbidity meter (HF Scientific).

Four bacterial mixtures were used in this test, and two dosing levels were implemented within each treatment: either 30 ml or 100 ml of a mixture per aquarium. Three replicates of each mix/dose combination were tested, along with three control aquaria which did not receive a bacterial mixture; totaling 27 test aquaria (i.e., (4×2×3)+3=27). Conditions for the various bacterial mixtures were as follows:

1) BC5—a bacterial mixture which had been under culture for 553 days preceding the test. A positive result with this mixture would demonstrate the long-term viability of the bacteria under culture conditions and the appropriateness of the culture techniques;

2) Rtr3—a bacterial mixture which had been bottled and stored in the dark for 118 days preceding the test. A positive result with this mixture would demonstrate that the storage method is valid and the mixture retains its viability for at least 119 days of storage;

3) Rtr4—a bacterial mixture which had been bottled and stored in the dark for 118 days preceding the test. A positive result with this mixture would demonstrate that the storage method is valid and the mixture retains its viability for at least 119 days of storage;

4) Rtr7—a bacterial mixture which had been grown from an inoculum from BC5. A positive result with this mixture would demonstrate that one can culture the bacterial consortium in the mixture for successive generations and it maintains its viability.

The test continued for 23 days, at the termination of which the ammonia and nitrite concentrations in the aquaria were virtually 0 mg/L. There were significant differences among the mean highest ammonia and nitrite concentrations for the various aquaria, as well as the length of time necessary for the aquaria to reach a 0 mg/L concentration. Other differences between the bacterial mixtures are depicted in Table 11.

TABLE 14

Detection of Ammonia-Oxidizing Bacteria

| Template | Type A AOB PCR | Type B AOB PCR | Type C AOB PCR |
|---|---|---|---|
| R7c140 (TypeA) | +++ | − | − |
| R7c187 (TypeA) | +++ | − | − |
| R3c5 (TypeB) | − | +++ | − |

TABLE 14-continued

Detection of Ammonia-Oxidizing Bacteria

| Template | Type A AOB PCR | Type B AOB PCR | Type C AOB PCR |
|---|---|---|---|
| R5c20 (TypeB) | – | +++ | – |
| R3c12 (TypeC) | – | – | +++ |
| R5c47 (TypeC) | – | – | +++ |
| N. europaea | – | – | – |
| N. multiformis | – | – | – |
| N. cryotolerans | – | – | – |
| BC5 Pre BA 6 | – | – | – |
| BC5 Post BA 6 | + | – | – |
| R3 Pre BA6 | + | + | +/– |
| R3 Post BA 6 | + | +/– | – |
| R4 Pre BA6 | + | + | – |
| R4 Post BA 6 | ++ | – | – |
| R5 Pre BA 7 | – | ++ | ++ |
| R5 Post BA7 | – | – | – |
| R7 Pre BA6 | ++ | + | – |
| R7 Post BA 6 | ++ | – | – |
| R7 Pre BA7 | + | +/– | – |
| R7 Post BA7 | ++ | – | – |
| Cycle | – | – | – |
| Fritzyme | – | – | – |
| Stresszyme | – | – | – |
| Cryst Clr Nitrifier | – | – | – |
| Cryst Clr Bio Clar L | – | – | – |
| Cryst Clr Bio Clar S | – | – | – |
| Acqmar Phospaht | – | – | – |
| Trop Sci Sludge | – | – | – |
| Trop Sci Rapid Act | – | – | – |

+++ very strong presence, clearly indicates high amount of target organism
++ strong presence, indicates significant detection of signal
+ clear presence, signal detected
=/– possible presence, signal weak but above background
– no presence/signal detected

TABLE 15

Results of Bacterial Additives Test VI.

| Bacterial Mixture | Time to ≤0.50 mg/L (days) | | Mean Maximum Concentration (mg/L-N) | |
|---|---|---|---|---|
| | Ammonia | Nitrite | Ammonia | Nitrite |
| Rtr7 - 100 ml | 6 | 7 | 1.1 | 1.4 |
| Rtr3 - 100 ml | 7 | 11 | 1.9 | 3.4 |
| Rtr7 - 30 ml | 7 | 10 | 1.9 | 3.7 |
| BC5 - 100 ml | 8 | 18 | 2.4 | 4.5 |
| Rtr4 - 100 ml | 8 | 8 | 2.7 | 0.6 |
| Rtr3 - 30 ml | 9 | 15 | 3.1 | 5.9 |
| Rtr4 - 30 ml | 9 | 10 | 2.9 | 2.1 |
| BC5 - 30 ml | 10 | 21 | 4.1 | 8.9 |
| Control | 12 | 23 | 4.9 | 13.4 |

Figure 4:
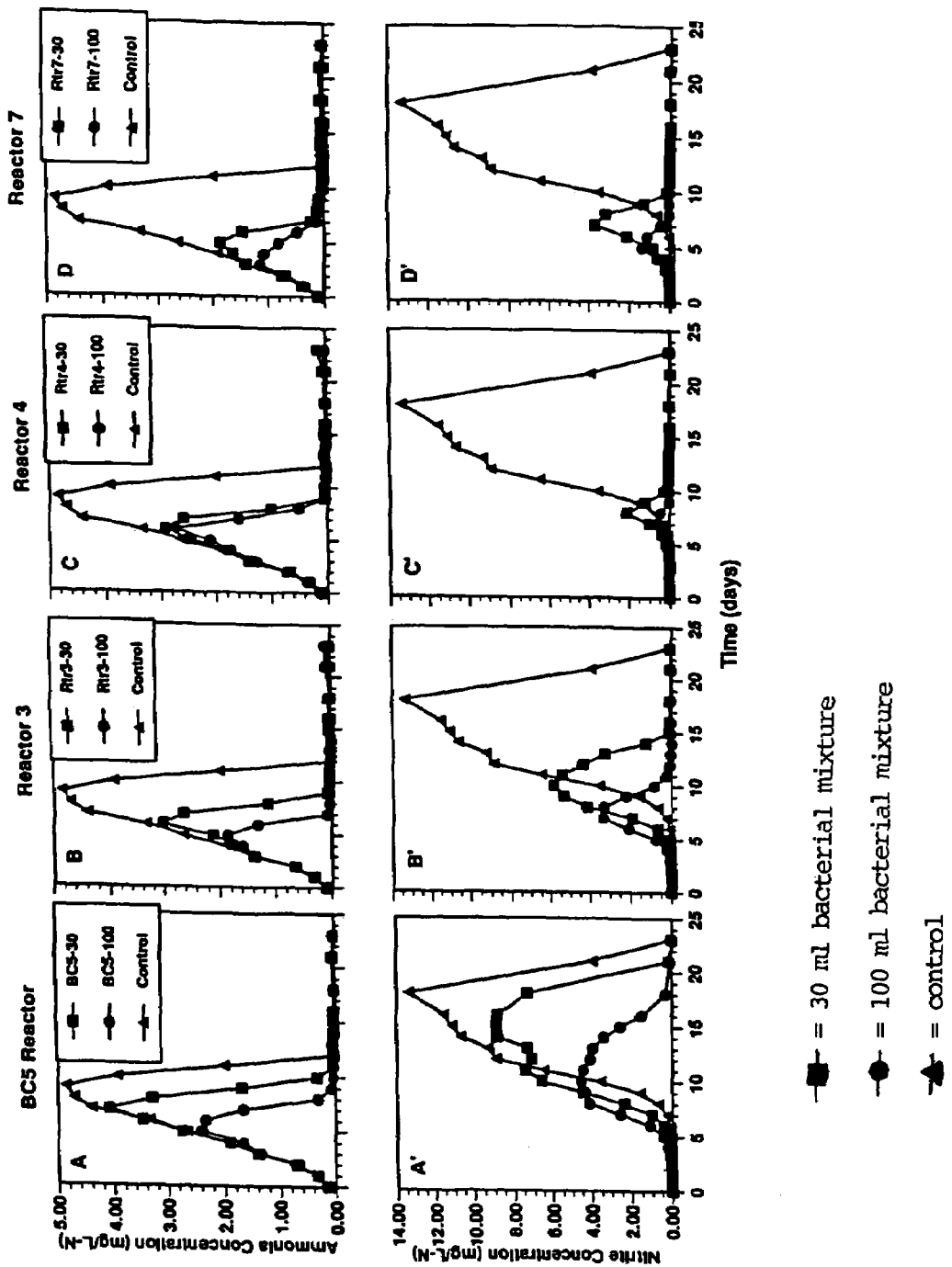
FIG. 4 (A-D') illustrates mean ammonia and nitrite trends for the Bacterial Additives VI test for the bacterial strains represented by SEQ ID NO:1, SEQ ID NO:2, SEQ ID NO:3 and SEQ ID NO:4, in accordance with an embodiment of the present invention.

FIG. 4 shows the mean ammonia and nitrite concentrations over the test period for the four mixtures along with the controls. For the BC5 mixture, ammonia reached 0 mg/L on day 8 for the aquaria dosed with 100 ml of BC5 mixture and day 10 for the aquaria dosed with 30 ml of BC5 mixture. The ammonia concentration in the control aquaria did not reach 0 mg/L until day 12. The highest mean ammonia concentration reached for the control aquaria was 4.9 mg/L. However, for aquaria dosed with 30 ml of the BC5 bacterial mixture, the highest mean ammonia concentration was 4.1 mg/L, while in the aquaria dosed with 100 ml of the BC5 bacterial mixture, the highest mean ammonia concentration was 2.4 mg/L. Thus, the addition of the BC5 bacterial mixture to newly set-up aquaria resulted in less ammonia exposure to the fish.

The ammonia exposure curve area values for the aquaria dosed with 30 ml or 100 ml of the BC5 mixture were 67% and 37% of the control aquaria curve area value, respectively (Table 16); 1.5 and 2.7 times less exposure to ammonia, respectively, for fish in the treatment aquaria.

TABLE 16

Toxicity Exposure Data for Bacterial Additives VI test.

| | Ammonia | | | | Nitrite | | |
|---|---|---|---|---|---|---|---|
| Treatment | Exposure Value | % of Control | Area | Treatment | Exposure Value | % of Control | Area |
| Rtr7-100 | 5.7 | 17% | 5.34 | Rtr4-100 | 60.9 | 2% | 1.99 |
| Rtr3-100 | 3.9 | 26% | 7.87 | Rtr7-100 | 25.5 | 4% | 4.75 |
| Rtr7-30 | 3.6 | 28% | 8.59 | Rtr4-30 | 20.2 | 5% | 6.01 |
| BC5-100 | 2.7 | 37% | 11.34 | Rtr7-30 | 9.7 | 10% | 12.45 |
| Rtr4-100 | 2.7 | 38% | 11.47 | Rtr3-100 | 8.8 | 11% | 13.81 |
| Rtr4-30 | 2.2 | 45% | 13.70 | Rtr3-30 | 3.6 | 28% | 33.73 |
| Rtr3-30 | 2.2 | 45% | 13.71 | BC5-100 | 3.1 | 33% | 39.37 |
| BC5-30 | 1.5 | 67% | 20.38 | BC5-30 | 1.3 | 75% | 90.56 |
| Control | 1.0 | 100% | 30.56 | Control | 1.0 | 100% | 121.13 |

Nitrite concentrations reached 0 mg/L by day 18 in aquaria dosed with 100 ml of BC5 mixture, by day 21 in aquaria dosed with 30 ml of BC5 mixture, and by day 23 in control aquaria. The control aquaria reached a mean maximum nitrite control of 13.4 mg/L, while aquaria dosed with 30 ml of the BC5 mixture had a mean maximum nitrite concentration of 8.9 mg/L and those dosed with 100 ml of BC5 mixture had a maximum nitrite concentration of only 4.5 mg/L (Table 15; FIG. 4).

The nitrite exposure curve area values for the aquaria dosed with 30 ml or 100 ml of the BC5 mixture were 75% and 33% of the control aquaria curve area value, respectively (Table 16); 1.3 and 3.1 times less exposure to nitrite, respectively, for fish in the treatment aquaria.

Aquaria including bacterial mixture Rtr3, which had been stored for 118 days, established nitrification faster than did control aquaria. The mean maximum ammonia concentration for the aquaria dosed with 30 ml or 100 ml of the Rtr3 mixture was 3.1 and 1.9 mg/L, respectively (Table 15). In contrast, the control aquaria demonstrated a mean maximum ammonia concentration of 4.9 mg/L. The control aquaria reached a 0 mg/L ammonia concentration after 12 days, while the aquaria dosed with 30 ml or 100 ml of the Rtr3 bacterial mixture took only 9 and 7 days to reach 0 mg/L, respectively (Table 15).

The mean maximum nitrite concentration was 13.4 mg/L in the control aquaria, while the mean maximum nitrite concentration in aquaria dosed with 30 ml or 100 ml of the Rtr3 bacterial mixture was only 5.9 mg/L and 3.4 mg/L, respectively. The control aquaria reached a 0 mg/L nitrite concentration in 23 days, while the aquaria dosed with 30 ml or 100 ml of Rtr3 bacterial mixture reach 0 mg/L after only 15 and 11 days, respectively (Table 15).

The ammonia exposure curve area values for the aquaria dosed with 30 ml or 100 ml of the Rtr3 mixture were 45% and 26% of the control aquaria curve area value, respectively (Table 15); 2.2 and 3.9 times less exposure to ammonia, respectively, for fish in the treatment aquaria.

The nitrite exposure curve area values for the aquaria dosed with 30 ml or 100 ml of the Rtr3 mixture were 28% and 11% of the control aquaria curve area value, respectively (Table 15); 3.6 and 8.8 times less exposure to nitrite, respectively, for fish in the treatment aquaria.

For the aquaria dosed with the Rtr4 mixture, the mean maximum ammonia concentration was 2.9 mg/L and 2.7 mg/L, respectively, for a dosage volume of 30 ml and 100 ml (Table 15), while control aquaria reached a mean maximum ammonia concentration of 4.9 mg/L. The ammonia exposure curve area values for the aquaria dosed with 30 ml or 100 ml of the Rtr4 mixture were 45% and 38% of the control aquaria curve area value, respectively. These values show that the addition of the mixture resulted in 2.2 and 2.7 times less exposure to ammonia, respectively, for the fish in the treatment aquaria when compared to the control aquaria (Table 15). Aquaria dosed with 30 ml of the Rtr4 mixture completed the nitrification cycle in 10 days, while nitrification was established in 8 days for aquaria dosed 100 ml of the Rtr4 mixture (Table 15). Nitrification was established in 23 days in the control aquaria.

The mean maximum nitrite concentration for the aquaria dosed with 30 ml or 100 ml of the Rtr4 bacterial mixture was 2.1 mg/L and 0.6 mg/L, respectively. The control aquaria had a mean maximum nitrite concentration of 13.4 mg/L.

The nitrite exposure curve area values for the aquaria dosed with 30 ml or 100 ml of the Rtr4 mixture were 5% and 2% of the control aquaria curve area value, respectively; 20.2 and 60.9 times less exposure to nitrite, respectively, for fish in treatment aquaria (FIG. 4; Table 15).

The bacterial mixture Rtr7, which was a subculture from the BC5 mixture, demonstrated a significantly faster establishment of nitrification when compared to the control aquaria. The control aquaria took 12 days to reach a 0 mg/L ammonia concentration, while aquaria dosed with 30 ml or 100 ml of the Rtr7 bacterial mixture took only 7 and 6 days, respectively (Table 15). The mean maximum ammonia concentration for aquaria dosed with 30 ml or 100 ml of the R7 mixture was 1.9 mg/L and 1.1 mg/L, respectively. This is in contrast to the control aquaria that had a mean maximum ammonia concentration of 4.9 mg/L (Table 15).

The nitrite concentration reached a mean maximum concentration of 13.4 mg/L in the control aquaria, while in aquaria dosed with 30 ml or 100 ml of the Rtr7 bacterial mixture the mean maximum nitrite concentration was only 3.7 mg/L and 1.4 mg/L, respectively (Table 15). Control aquaria reached a 0 mg/L nitrite concentration in 23 days, while aquaria dosed with 30 ml or 100 ml took only 10 and 7 days, respectively, to reach 0 mg/L (Table 15; FIG. 4).

The ammonia exposure curve area values for aquaria dosed with 30 ml or 100 ml of the Rtr7 mixture were 28% and 17% of the control aquaria curve area value, respectively (Table 15); 3.6 and 5.7 times less exposure to ammonia, respectively, for fish in the treatment aquaria.

The nitrite exposure curve area values for aquaria dosed with 30 ml or 100 ml of the Rtr7 mixture were 10% and 4% of the control aquaria curve area value, respectively; 5.7 and 25.5 times less exposure to nitrite, respectively, for fish in the treatment aquaria (Table 15).

In summary, the data from the test show that the various bacterial mixtures of the present invention accelerate the establishment of nitrification in aquaria. Use of these mixtures in aquaria significantly reduced the degree of ammonia and nitrite exposure to fish. The results further demonstrate that a mixture can be viably maintained over a long period of time (e.g., BC5), that the mixture can be stored for several months (e.g., Rtr 3 and Rtr 4) and that successive generations of the mixture retain their nitrifying ability (e.g., Rtr 7).

Example 13

Bacterial Additive Test VII

The goal of this test was to evaluate two mixtures of bacterial stains of the present invention as they may be implemented in a "real world" setting while comparing their performance to that of commercial bacterial mixtures.

In general, a new aquarium owner first purchases the necessary equipment for setting-up an aquarium able to maintain aquatic life. The equipment may include the aquarium itself, decorations, a heater and filter, and a water conditioner. The aquarium is then assembled and filled with water, the filters are started, the heater is adjusted to the proper water temperature and the water conditioner added to remove chlorine. At this point, the fish are usually added, but there may be insufficient populations of ammonia- and nitrite-oxidizing bacteria present to maintain the ammonia and nitrite concentrations in the aquarium at biologically safe (i.e., non-toxic) concentrations (e.g., below 0.5 mg/L-N). Therefore, the newly set-up aquarium will exhibit what is commonly referred to as "new tank syndrome" (i.e., elevated concentrations of ammonia and nitrite in the first several weeks after setting-up a new aquarium when an insufficient population of nitrifying bacteria are present to maintain safe ammonia and nitrite concentrations).

To at least partially alleviate new tank syndrome, a bottled mixture of microorganisms or an enzyme mix (i.e., the bacterial mixture) may be purchased and introduced to the new aquarium to accelerate, or in some cases, eliminate new tank syndrome. In theory, introduction of the bottled mixture should result in comparatively lower ammonia and nitrite concentrations in an aquarium during its initial weeks than in the absence of such a mixture. Also, less time should be required for the ammonia and nitrite concentrations to reach 0 mg/L.

Thirty-three ten-gallon aquaria and thirty-three Penguin 170B (Marineland Aquarium Products) hang-on-the-back style power filters were sterilized, thoroughly rinsed and allowed to air dry. Each aquarium was filled with 10 lbs. of rinsed aquarium gravel (RMC Lonestar #3) and the filter set-up on the back. Next, each aquarium was filled with 35 L of city water, which had been pre-filtered through activated carbon, and the water level marked on each aquarium. This mark was used as a guide to indicate when aquaria water needed to be topped-off to account for water lost due to evaporation or sampling. Deionized water was used for topping-off the aquaria. The filters were allowed to run overnight prior to the addition of bacterial additives and fish.

On the first day of the test, the aquaria were topped off with deionized water to account for water and a baseline water sample. Carbon cartridges (Marineland Aquarium Products, Part No. PA 0133) were rinsed with tap water and placed in each filter. New BIOWHEELS (Marineland Aquarium Products, Part No. PR 1935B) were placed in each filter. After thirty minutes each tank was dosed with its designated bacterial additive. The dosages were as described in Table 17. Thirty minutes after the bacterial additives were added, a second set of water samples were extracted for analysis. Six assorted barbs [(*Puntius conchonius*) Rosy Barbs; (*Puntius tetrazona*) Albino Tiger Barbs and Tiger Barbs] were then added to each tank. The fish in each aquarium were fed twice a day (at about 9:00 a.m. and again at 4:30 p.m.) with a total of 0.4 grams of tropical fish flakes per day.

Water samples were collected and analyzed tested daily for pH, ammonia, nitrite and conductivity. On Monday, Wednesday and Friday the water was tested for nitrate and turbidity. Anions and cations were measured periodically. Measurements for pH were made with a Denver Instruments Model 225 pH/Ion meter equipped with a Denver Instruments pH combination electrode. A Tecator FIAstar 5010 Analyzer was used to measure ammonia, nitrite and nitrate (as nitrogen) using methods described in Tecator Application Notes. Cations (sodium, ammonium-nitrogen, potassium, magnesium and calcium) were analyzed using a Dionex DX500 System with a CS15 4-mm Analytical Column. Specific conductance was measured directly in each tank at approximately 12:30 p.m. daily using a YSI Model 30 hand-held salinity, conductivity and temperature system. Turbidity data was determined with a DRT-100 turbidity meter (HF Scientific).

Two formulations containing bacterial strains of the present invention were tested along with four commercially available bacterial mixtures. On the first day of the test, 100 ml of the first formulation (Rtr5) was added to each of four aquaria, and 100 ml of the second formulation (Rtr7) was added to another four aquaria.

The commercially available bacterial mixtures were dosed according to manufacturer's instructions, for the treatments of BIOZYME, CYCLE, FRITZ-ZYME NO.7 and STRESS ZYME. Furthermore, each of these commercially available bacterial mixtures was also tested at three times the recommended dosing level (Table 17). There were four replicate aquaria per treatment/dosage combination for a total of 33 aquaria (i.e., (((4×3)×2)+(2×3)+3)=33).

Figure 5:
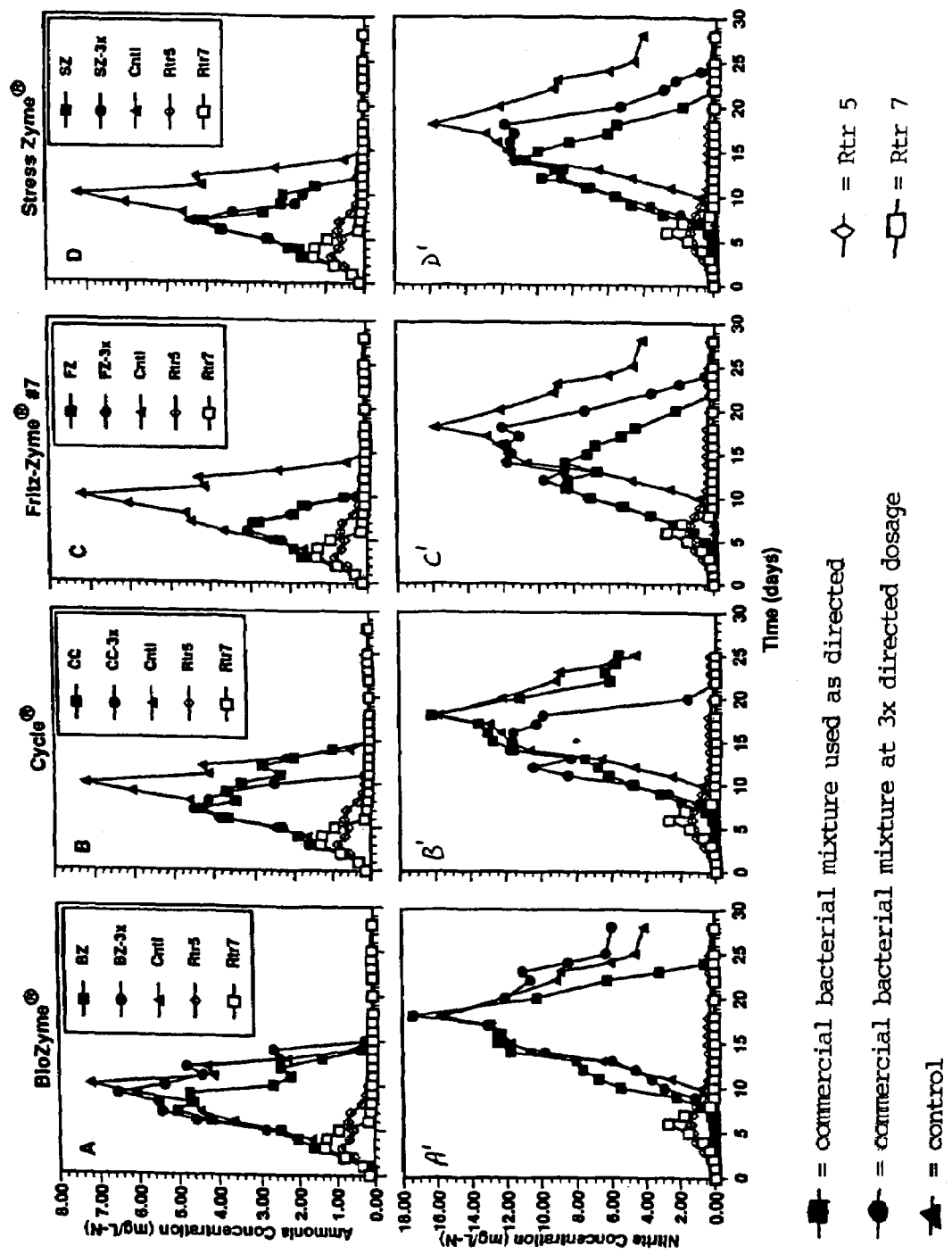
FIG. 5 (A-D') illustrates mean ammonia and nitrite trends for the Bacterial Additives VII test for the bacterial strains represented by SEQ ID NO:1, SEQ ID NO:2, SEQ ID NO:3 and SEQ ID NO:4, in accordance with an embodiment of the present invention.

The ammonia and nitrite trends for the treatments and control for Bacterial Additives Test VII are shown in FIG. 5. For clarity of presentation, each of the commercially available bacterial mixtures tested is presented with the control and the two test mixtures containing the bacterial strain of the present invention. The scale of each plot is the same so comparisons between all the treatments can be easily made. The data show that the Rtr5 and Rtr7 mixtures, containing the bacterial stains of the present invention, significantly decreased the time necessary to establish nitrification in newly set-up aquaria compared to aquaria that were not dosed (i.e., the controls) or which received a commercially available bacterial mixture. Furthermore, the maximum ammonia and nitrite concentrations reached in the aquaria which were dosed with either the Rtr5 or the Rtr7 bacterial mixture were significantly lower than all other treatments (FIG. 5; Table 18).

TABLE 18

Results of Bacterial Additives Test VII

| Bacterial Mixture | Time to ≦0.50 mg/L (days) | | Mean Maximum Conc. (mg/L-N) | |
|---|---|---|---|---|
| | Ammonia | Nitrite | Ammonia | Nitrite |
| Rtr7 | 6 | 8 | 2.8 | 1.3 |
| Rtr5 | 8 | 10 | 1.5 | 0.9 |
| FRITZ-ZYME (3×) | 10 | 24 | 8.5 | 3.1 |
| FRITZ-ZYME | 11 | 22 | 7.2 | 3.1 |
| CYCLE (3×) | 11 | 22 | 8.4 | 4.5 |
| STRESS ZYME | 12 | 22 | 8.3 | 4.1 |
| STRESS ZYME (3×) | 12 | 25 | 8.6 | 4.3 |
| BIOZYME | 14 | 25 | 8.6 | 5.1 |
| BIOZYME (3×) | 15 | 30+ | 8.8 | 6.5 |
| CYCLE | 15 | 30 | 8.8 | 4.3 |
| Control | 15 | 30 | 8.9 | 7.2 |

The Rtr5 and Rtr7 mixtures established nitrification in newly set-up aquaria significantly faster than the commercial mixtures and untreated aquaria. Complete nitrification was established in 8 days with the Rtr7 mixture and in 10 days with the Rtr5 mixture (Table 18). The closest treatments to these were FRITZ-ZYME at the its normal dosing level, CYCLE at three times its normal dosing level, and STRESS ZYME at its normal dosage level; each of which took 22 days (Table 18). The Rtr5 and Rtr7 mixtures were therefore 2.2 to 2.8 times faster at establishing nitrification then these other mixtures.

The difference in the maximum concentration of ammonia or nitrite reached for the various mixtures and control were also significantly different (Table 18). The mean (N=3) maximum ammonia concentration of 1.5 mg/L reached during the test for the Rtr5 mixture was 4.8 times less than the FRITZ-ZYME (mean 7.2 mg/L, N=3), dosed at its normal level, which was the nearest commercially available mixture (Table 18). The mean maximum nitrite concentration for the Rtr5 mixture was 0.9 mg/L. Again, FRITZ-ZYME dosed at its normal level was the closest commercially available mixture with a mean maximum nitrite concentration of 3.1 mg/L. Therefore, the Rtr5 mixture was 3.4 times more effective at establishing nitrification then the presently available commercial mixtures tested.

The Rtr7 mixture exhibited the same trend as the Rtr5 mixture in that aquaria dosed with this mixture exhibited significantly lower maximum ammonia-nitrogen and nitrite-nitrogen concentrations than aquaria dosed with commercially available bacterial mixtures (Table 18). The Rtr7 mixture had mean maximum ammonia and nitrite concentrations of 2.8 mg/L and 1.3 mg/L, respectively. These were 2.6 and 2.4 times lower, respectively, than the closest commercially available bacterial mixture (FRITZ-ZYME, dosed at its normal level) (FIG. 5; Table 18).

In terms of the exposure curves, the bacterial mixtures Rtr5 and Rtr7, which incorporate bacterial strains of the present invention, significantly outperformed the commercially available mixtures (Table 19). In particular, Rtr7 performed better than any mixture with the fish exposed to just 13% of the ammonia and 5% of the nitrite of the control. Rtr5 was almost as effective, with ammonia exposure at 14% of control levels and nitrite exposure at 9% of the control (Table 19). These results mean that fish in aquaria receiving either Rtr7 or Rtr5 are exposed to 7.3 to 7.6 times less ammonia and 11.6 to 19.6 times less nitrite than fish in control aquaria. After Rtr7 and Rtr5, the next best mixtures reduced the exposure of ammonia and nitrite by only 50% when compared to controls (Table 19).

taken. Each tank was dosed with one bacterial treatment, however no bacterial mixture was added to the control group.

There were four treatments for this test: Reactor 3 included strains of AOB of the present invention represented by SEQ ID NO:1, SEQ ID NO:2, and SEQ ID NO:3; Reactor 29 included strains of AOB of the present invention represented by SEQ ID NO:18, SEQ ID NO:19 and sequences from two *halophila*-like strains; CYCLE (a commercially available bacterial mixture for use in freshwater or saltwater); and STRESS ZYME (another commercially available bacterial mixture for use in freshwater or saltwater). Each treatment had three replicates. Aquaria receiving the Reactor 3 and Reactor 29 treatments were dosed with 100 ml of either mixture one time on the first day of the test. Aquaria receiving the CYCLE or STRESS ZYME treatments were dosed with 10 ml of either treatment on the first day of the test, an additional 10 ml on day 7 of the test and an additional 5 ml every 7 days after that for the duration of the test. Four assorted damsels (*Pomacentrus* spp.) were added to each tank on the first day of the test and fed twice a day.

TABLE 19

Toxicity exposure data for the Bacterial Additives VII test.

| | Ammonia | | | | Nitrite | | |
|---|---|---|---|---|---|---|---|
| Treatment | Exposure Value | % of control | Area | Treatment | Exposure Value | % of control | Area |
| Rtr7 | 7.6 | 13% | 5.90 | Rtr7 | 19.6 | 5% | 8.16 |
| Rtr5 | 7.3 | 14% | 6.11 | Rtr5 | 11.6 | 9% | 13.85 |
| Fritz 3x | 2.6 | 39% | 17.52 | Fritz 1x | 1.9 | 52% | 82.71 |
| Fritz 1x | 2.5 | 40% | 17.84 | Stress 1x | 1.8 | 55% | 88.08 |
| Stress 3x | 1.9 | 52% | 23.50 | Cycle 3x | 1.6 | 63% | 100.05 |
| Stress 1x | 1.9 | 53% | 23.76 | Stress 3x | 1.3 | 75% | 119.42 |
| Cycle 3x | 1.7 | 59% | 26.36 | Fritz 3x | 1.2 | 84% | 134.60 |
| Cycle 1x | 1.3 | 76% | 34.03 | Bio 1x | 1.1 | 88% | 141.50 |
| Bio 1x | 1.3 | 79% | 35.29 | Control | 1.0 | 100% | 159.97 |
| Control | 1.0 | 100% | 44.82 | Cycle 1x | 1.0 | 104% | 166.83 |
| Bio 3x | 0.9 | 111% | 49.90 | Bio 3x | 0.9 | 114% | 182.30 |

Example 14

Bacterial Additive Test VIII

The goal of this test was to evaluate various mixtures of AOB strains of the present invention as they may be implemented in a "real world" setting. The performance of these mixtures of the present invention were compared to other AOB strains of the present invention, as well as to commercially available bacterial mixtures that claim they are suitable for use in either freshwater or saltwater aquaria.

For this test, fifteen 10-gallon aquaria and fifteen Penguin 170B (Marineland Aquarium Products) hang-on-the-back style power filters were sterilized, thoroughly rinsed and allowed to air dry. On the following day each tank was filled with 10 lbs. of rinsed Tideline Crushed Coral #5 and equipped with a sterilized power filter (PF 0170B) and rinsed carbon cartridge. Each tank was filled with 35 L of artificial seawater. The seawater was a combination of Tropic Marine salt mix and post GAC water to a salinity of 30 ppt. The filters were allowed to run overnight prior to the addition of bacterial additives and fish.

The next morning the tanks were topped off with ultrapure water to compensate for evaporation and water samples Water samples were collected and analyzed daily for pH, ammonia, nitrite and conductivity. On Monday, Wednesday and Friday the water was tested for nitrate and turbidity. Measurements for pH were made with a Denver Instruments Model 225 pH/Ion meter equipped with a Denver Instruments pH combination electrode. A Tecator FIAstar 5010 Analyzer was used to measure ammonia, nitrite and nitrate (as nitrogen) using methods described in Tecator Application Notes. Salinity was measured directly in each tank daily using a YSI Model 30 hand-held salinity, conductivity and temperature system. Turbidity data was determined with a DRT-100 turbidity meter (HF Scientific).

Figure 8:
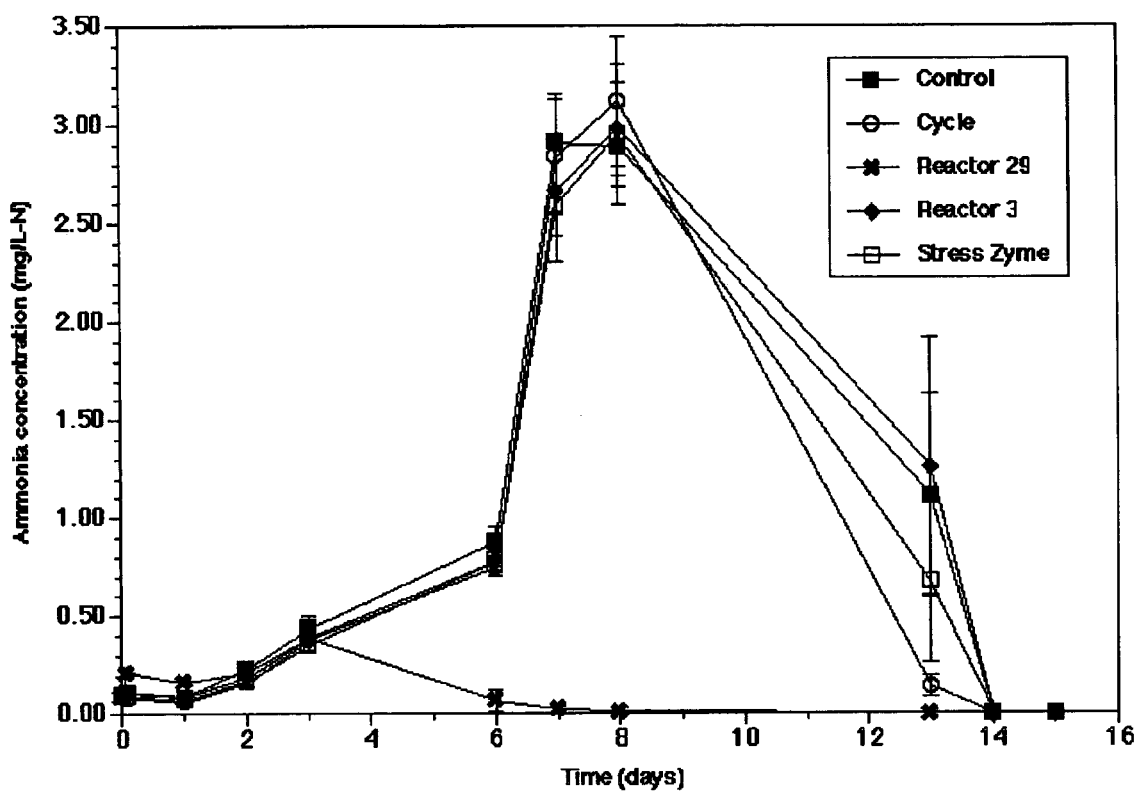
FIG. 8 illustrates mean ammonia concentration trends for the Bacterial Additives VIII test for freshwater bacterial strains represented by SEQ ID NO:1, SEQ ID NO:2, and SEQ ID NO:3 and seawater bacterial strains represented by SEQ ID NO:18, SEQ ID NO:19 and two *N. halophila*-like strains in accordance with an embodiment of the present invention along with two commercially available nitrifying bacteria mixtures.

The mean ammonia concentrations for the four treatments and control are depicted in FIG. 8. Treatment Reactor 29, which consisted of strains of AOB represented by SEQ ID NO:18, SEQ ID NO:19 and two *N. halophila*-like strains, oxidized ammonia markedly quicker than the other treatments. The mean maximum ammonia concentration of treatment Reactor 29 was also significantly lower than the other three treatments. In fact, the ammonia trend for the other three treatments over the first 14 days of newly set up aquaria were not significantly different than the control (non-inoculated) treatment. There was no evidence that adding more of the commercial AOB mixtures to the aquaria reduced the amount of time necessary to establish ammonia oxidation.

These results demonstrate several points: (1) the strains of AOB of the present invention represented by SEQ ID NO:1, SEQ ID NO:2, and SEQ ID NO:3 are different than the bacterial strains of the present invention represented by SEQ ID NO:18 and SEQ ID NO:19; (2) the AOB contained in the commercially available mixtures (reported to be *Nitrosomonas europaea*) are not effective at controlling ammonia during the start-up of new seawater aquaria; and (3) that the AOB represented by SEQ ID NO:18 and SEQ ID NO:19 are effective at controlling and maintaining ammonia concentrations in newly set-up seawater aquaria.

Example 15

Bacterial Additive Test IX

The goal of this test was to compare the biomass material from reactor SB7 (which contained AOB strains of the present invention represented by SEQ ID NO:18, SEQ ID NO:19 and two *halophila*-like strains) to aquaria that did not receive a bacterial inoculation.

For this test, eight 10-gallon aquaria and eight Penguin 170B (Marineland Aquarium Products) hang-on-the-back style power filters were sterilized, thoroughly rinsed and allowed to air dry. On the following day each tank was filled with 10 lbs. of rinsed Tideline Crushed Coral #5 and equipped with a sterilized power filter (PF 0170B) and rinsed carbon cartridge. Each tank was filled with 35L of artificial seawater. Artificial seawater was made by adding INSTANT OCEAN SeaSalts (Aquarium Systems, Mentor, Ohio) to carbon filtered city water until the salinity was 30 ppt. The aquaria were filled with the seawater and the filters were allowed to run overnight prior to the addition of bacterial additives and fish.

The next morning the tanks were topped off with ultrapure water to compensate for evaporation and water samples taken. Then four tanks were dosed with 150 ml of SB7 reactor bacterial mixture. The other four tanks were not dosed with a bacterial mixture. The SB7 AOB reactor mixture consisted of strains of AOB of the present invention represented by SEQ ID NO:18, SEQ ID NO:19 and two *N. halophila*-like strains. Six clownfish (*Amphiprion ocellaris*) were added to each tank on the first day of the test and fed twice a day. The fish feed was a mixture of frozen brine shrimp and Spirulina fish flakes. On Day 3 of the test, four additional clownfish (*Amphiprion ocellaris*) were added to each aquarium.

Water samples were collected and analyzed tested daily for pH, ammonia, nitrite and conductivity. On Monday, Wednesday and Friday the water was tested for nitrate and turbidity. Measurements for pH were made with a Denver Instruments Model 225 pH/Ion meter equipped with a Denver Instruments pH combination electrode. A Tecator FIAstar 5010 Analyzer was used to measure ammonia, nitrite and nitrate (as nitrogen) using methods described in Tecator Application Notes. Salinity was measured directly in each tank daily using a YSI Model 30 hand-held salinity, conductivity and temperature system. Turbidity data was determined with a DRT-100 turbidity meter (HF Scientific).

Figure 9:
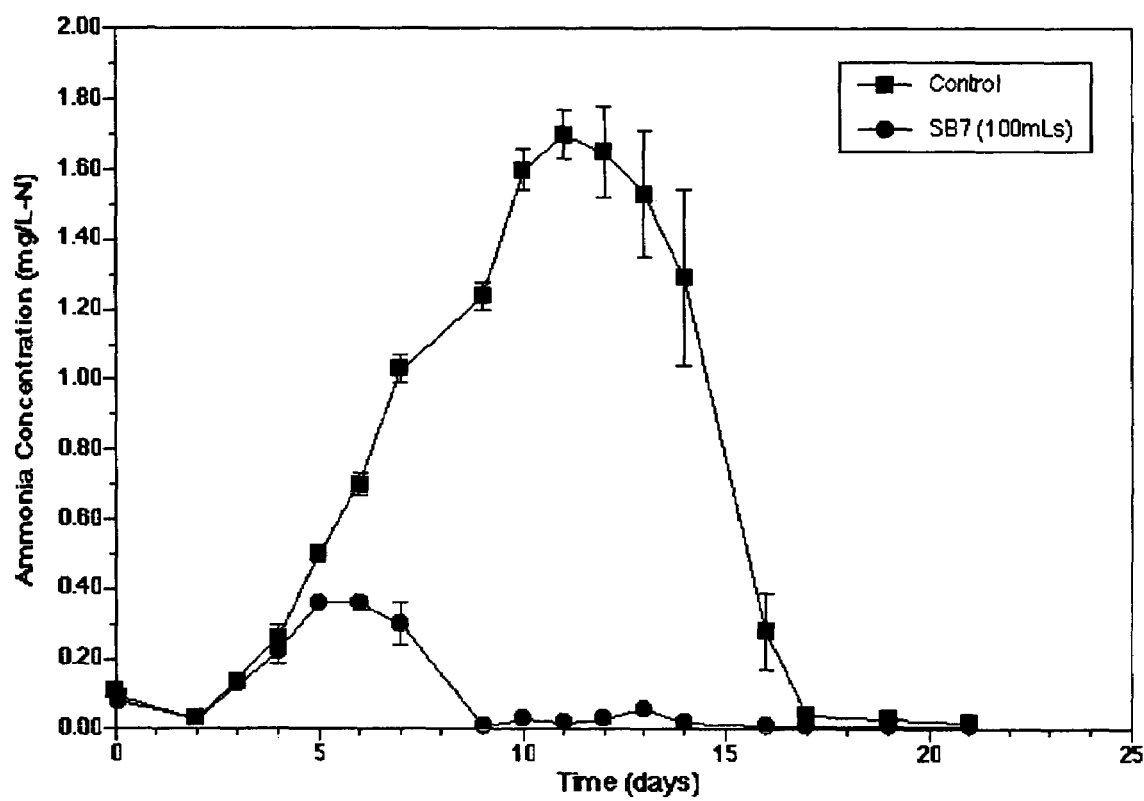
FIG. 9 illustrates mean ammonia concentration trends for aquaria in the Bacterial Additives IX test that were dosed with seawater bacterial strains represented by SEQ ID NO:18, SEQ ID NO:19 and two *N. halophila*-like strains in accordance with an embodiment of the present invention.

The mean ammonia concentrations for the SB7 treatment and control are presented in FIG. 9. SB7 treatment including strains of AOB of the present invention represented by SEQ ID NO:18, SEQ ID NO:19 and two *N. halophila*-like strains oxidized ammonia markedly quicker than did the control. The mean ammonia concentration reached 0 mg/L on day 9 in tanks receiving the SB7 treatment, while 17 days elapsed in the control aquaria before ammonia values reached the same level of 0 mg/L. Furthermore, the mean maximum ammonia concentration of the SB7 treatment (about 0.4 mg/L-N) was significantly lower than the control treatment (1.72 mg/L-N).

The results demonstrate that the strains of AOB of the present invention represented by SEQ ID NO:18 and SEQ ID NO:19 are effective at controlling ammonia concentrations in newly set-up seawater aquaria.

Example 16

Bacterial Additive Test X

The goal of this test was to compare the biomass material from reactor SB7 (which contained AOB strains of the present invention represented by SEQ ID NO:18, SEQ ID NO:19 and two *N. halophila*-like strains) and reactor B7 (which contained two *N. halophila*-like AOB strains) to aquaria that received no bacterial inoculation.

For this test, twelve 10-gallon aquaria and twelve Penguin 170B (Marineland Aquarium Products) hang-on-the-back style power filters were sterilized, thoroughly rinsed and allowed to air dry. On the following day each tank was equipped with a sterilized power filter (PF 0170B) and rinsed carbon cartridge. Each tank was filled with 19 L of artificial seawater. Artificial seawater was made by adding INSTANT OCEAN SeaSalts (Aquarium Systems, Mentor, Ohio) to carbon filtered city water until the salinity was 29 ppt. The aquaria were filled with the seawater and the filters were allowed to run overnight prior to the addition of bacterial additives and ammonia.

The next morning the tanks were topped off with ultrapure water to compensate for evaporation and water samples taken. Each treatment and the control aquaria had four replicates. Four aquaria were dosed with 150 ml of SB7 reactor bacterial mixture, four aquaria were dosed with 150 ml of B7 reactor bacterial mixture, and four aquaria were not dosed with any bacterial mixture. The SB7 AOB reactor mixture consisted of strains of AOB of the present invention represented by SEQ ID NO:18, SEQ ID NO:19 and two *N. halophila*-like strains. The B7 AOB reactor mixture consisted of two *N. halophila*-like strains of AOB.

Each day 11.5 mg of ammonia-nitrogen was added to each aquarium. Water samples were collected and analyzed tested daily for pH, ammonia, nitrite and conductivity. On Monday, Wednesday and Friday the water was tested for nitrate and turbidity. Measurements for pH were made with a Denver Instruments Model 225 pH/Ion meter equipped with a Denver Instruments pH combination electrode. A Tecator FIAstar 5010 Analyzer was used to measure ammonia, nitrite and nitrate (as nitrogen) using methods described in Tecator Application Notes. Salinity was measured directly in each tank daily using a YSI Model 30 hand-held salinity, conductivity and temperature system. Turbidity data was determined with a DRT-100 turbidity meter (HF Scientific).

Figure 10:
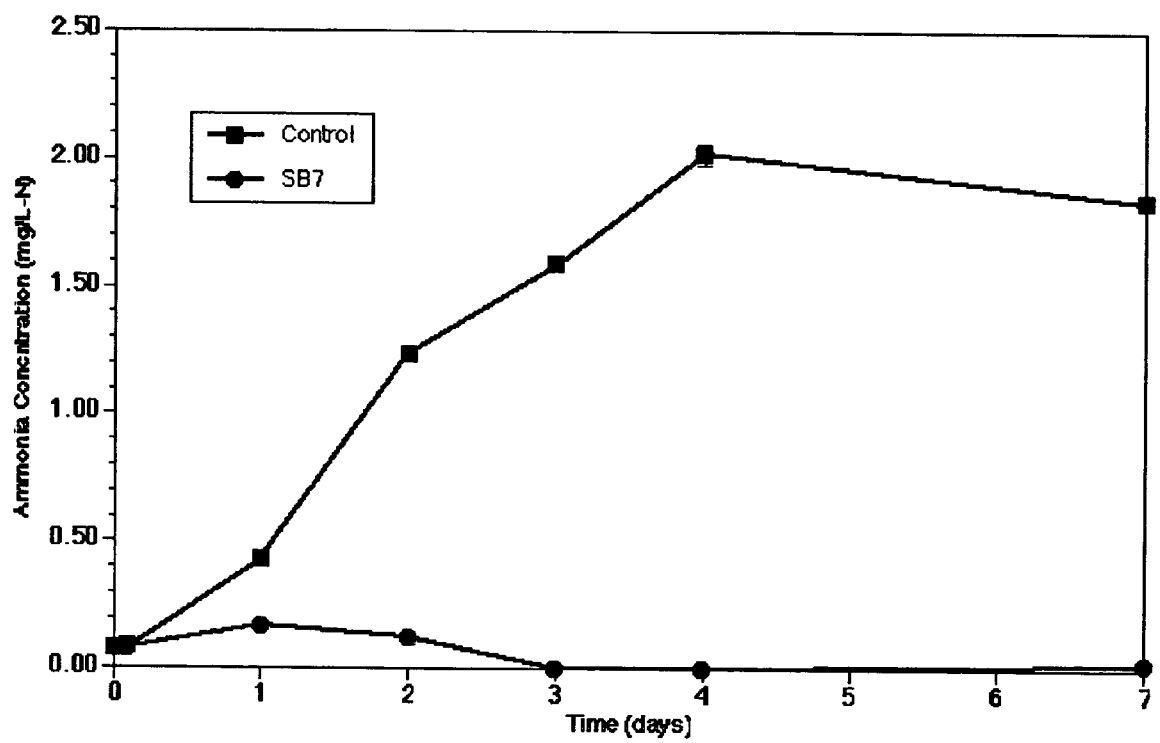
FIG. 10 illustrates mean ammonia concentration trends for the Bacterial Additives X test. Two bacterial mixtures of seawater bacterial strains represented by SEQ ID NO:18, SEQ ID NO:19 and two *N. halophila*-like strains were tested against non-inoculated aquaria in accordance with an embodiment of the present invention.

The mean ammonia concentrations for the two treatments and control are depicted in FIG. 10. The ammonia values for the aquaria that received either reactor B7 or reactor SB7 treatment oxidized ammonia at nearly the same rate; markedly faster than the control. The mean ammonia concentration reached 0 mg/L on day 3 for the tanks receiving either the B7 or SB7 treatments, and the mean maximum ammonia concentration of the B7 and SB7 treatment (about 0.2 mg/L-N) was significantly lower than the control treatment (2.0 mg/L-N) (FIG. 9).

The results demonstrate that the strains of AOB of the present invention represented by SEQ ID NO:18 and SEQ ID NO:19 are effective at controlling ammonia concentrations in newly set-up seawater aquaria.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A composition comprising an isolated bacterial strain that oxidizes ammonia to nitrite, wherein said bacterial strain comprises the nucleotide sequence set forth in SEQ ID NO:18.

2. The composition of claim 1 wherein the composition is in a form selected from the group consisting of liquid, frozen, freeze-dried and powdered.

3. The composition of claim 1, wherein the composition is included in a polymer.

4. The composition of claim 3, wherein the polymer is selected from the group consisting of acrylamide, alginate, carrageenan, and combinations thereof.

5. A composition comprising a concentrated bacterial strain that oxidizes ammonia to nitrite, wherein the 16S rDNA of the bacterial strain has a nucleotide sequence that has at least 96% identity over the full length thereof to SEQ ID NO:18, wherein hybridization of the 16S rDNA occurs under the following stringent conditions: hybridization in 20% to 30% formamide, 0.9 M NaCl, 0.01% sodium dodecyl sulphate, 20 mM Tris/HCl pH 7.4 at 46° C., and washing with 120 mM to 215 mM NaCl, 5 mM EDTA, 0.01% sodium dodecyl sulphate, and 20 mM Tris/HCl at 48° C.

6. The composition of claim 5 wherein said bacterial strain has a 16S rDNA sequence which is identical to SEQ ID NO:18.

7. The composition of claim 5, further comprising a microorganism selected from the group consisting of ammonia-oxidizing microorganisms, nitrite-oxidizing microorganisms, nitrate-reducing microorganisms, heterotrophic microorganisms, and combinations thereof.

8. An isolated nucleic acid consisting of: a nucleotide sequence that has at least 96% identity over the full length thereof to SEQ ID NO:18, wherein hybridization to SEQ ID NO:18 occurs under the following stringent conditions: hybridization in 30% formamide, 0.9 M NaCl, 0.01% sodium dodecyl sulphate, 20 mM Tris/HCl pH 7.4 at 46° C., and washing with 120 mM NaCl, 5 mM EDTA, 0.01% sodium dodecyl sulphate, and 20 mM Tris/HCl at 48° C.

9. The isolated nucleic acid of claim 8 wherein said sequence is identical to SEQ ID NO:18.

10. A composition comprising a bacterial strain that oxidizes ammonia to nitrite including the nucleotide sequence as set forth in SEQ ID NO:18 and at least one other bacterial strain that oxidizes ammonia to nitrite, wherein the at least one other bacterial strain has 16S rDNA including a nucleotide sequence independently selected from the group consisting of: a nucleotide sequence that has greater than 98% identity over the full length thereof to SEQ ID NO:3, a nucleotide sequence that has greater than 98% identity over the full length thereof to SEQ ID NO:4, a nucleotide sequence that has at least 96% identity over the full length thereof to SEQ ID NO:1, a nucleotide sequence that has at least 96% identity over the full length thereof to SEQ ID NO:2, a nucleotide sequence that has at least 96% identity over the full length thereof to SEQ ID NO:19 and a nucleotide sequence that has at least 96% identity over the full length thereof to SEQ ID NO:20, wherein hybridization of the 16S rDNA occurs under the following stringent conditions: hybridization in 20% to 30% formamide, 0.9 M NaCl, 0.01% sodium dodecyl sulphate, 20 mM Tris/HCl pH 7.4 at 46° C., and washing with 120 mM to 215 mM NaCl, 5 mM EDTA 0.01% sodium dodecyl sulphate, and 20 mM Tris/HCl at 48° C.

11. The composition of claim 10, said composition comprising a bacterial strain with a 16S rDNA including the nucleotide sequence as set forth in SEQ ID NO:1, a bacterial strain with a 16S rDNA including the nucleotide sequence as set forth in SEQ ID NO:2, a bacterial strain with a 16S rDNA iucluding the nucleotide sequence as set forth in SEQ ID NO:3, a bacterial strain with a 16S rDNA including the nucleotide sequence as set forth in SEQ ID NO:4, a bacterial strain with a 16S rDNA including the nucleotide sequence as set forth in SEQ ID NO:18, a bacterial strain with a 16S rDNA including the nucleotide sequence as set forth in SEQ ID NO:19 and a bacterial strain with a 16S rDNA including the nucleotide sequence as set forth in SEQ ID NO:20.

12. A composition comprising a bacterial strain that oxidizes ammonia to nitrite including the nucleotide sequence as set forth in SEQ ID NO:18 and at least one other bacterial strain that oxidizes ammonia to nitrite, wherein the at least one other bacterial strain has 16S rDNA including a nucleotide sequence independently selected from the group consisting of: the nucleotide sequence as set forth in SEQ ID NO:3, the nucleotide sequence as set forth in SEQ ID NO:4, the nucleotide sequence as set forth in SEQ ID NO:1, the nucleotide sequence as set forth in SEQ ID NO:2, the nucleotide sequence as set forth in SEQ ID NO:19 and the nucleotide sequence as set forth in SEQ ID NO:20.

* * * * *